(12) United States Patent
Bossenmaier et al.

(10) Patent No.: US 9,982,036 B2
(45) Date of Patent: May 29, 2018

(54) DUAL FC ANTIGEN BINDING PROTEINS

(75) Inventors: Birgit Bossenmaier, Seefeld (DE); Hubert Kettenberger, Munich (DE); Christian Klein, Bonstetten (CH); Klaus-Peter Kuenkele, Benediktbeuern (DE); Joerg-Thomas Regula, Munich (DE); Wolfgang Schaefer, Mannheim (DE); Manfred Schwaiger, Wang-Bergen (DE); Claudio Sustmann, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days. days.

(21) Appl. No.: 13/406,411

(22) Filed: Feb. 27, 2012

(65) Prior Publication Data

US 2012/0237506 A1 Sep. 20, 2012

(30) Foreign Application Priority Data

Feb. 28, 2011 (EP) ..................................... 11156320

(51) Int. Cl.
  *C07K 16/30* (2006.01)
  *C07K 16/28* (2006.01)
  *C07K 16/00* (2006.01)
  *C07K 16/32* (2006.01)

(52) U.S. Cl.
  CPC .......... *C07K 16/00* (2013.01); *C07K 16/2863* (2013.01); *C07K 16/32* (2013.01); *C07K 2317/41* (2013.01); *C07K 2317/64* (2013.01); *C07K 2317/66* (2013.01); *C07K 2317/732* (2013.01); *C07K 2317/76* (2013.01); *C07K 2317/77* (2013.01); *C07K 2317/92* (2013.01); *C07K 2317/94* (2013.01)

(58) Field of Classification Search
  None
  See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,677,425 A | 10/1997 | Bodmer et al. | |
| 5,731,168 A | 3/1998 | Carter et al. | |
| 5,747,654 A | 5/1998 | Pastan et al. | |
| 5,798,229 A | 8/1998 | Strittmatter et al. | |
| 5,821,333 A | 10/1998 | Carter et al. | |
| 5,959,083 A | 9/1999 | Bosslet et al. | |
| 6,166,185 A | 12/2000 | Davis et al. | |
| 6,239,259 B1 | 5/2001 | Davis et al. | |
| 6,511,663 B1 | 1/2003 | King et al. | |
| 6,558,672 B1 | 5/2003 | Pastan et al. | |
| 6,602,684 B1 | 8/2003 | Umana et al. | |
| 6,897,044 B1 | 5/2005 | Braslawsky et al. | |
| 6,946,292 B2 | 9/2005 | Kanda et al. | |
| 6,982,321 B2 | 1/2006 | Winter | |
| 7,129,330 B1 | 10/2006 | Little et al. | |
| 7,276,585 B2 | 10/2007 | Lazar et al. | |
| 7,317,091 B2 | 1/2008 | Lazar et al. | |
| 7,642,228 B2 | 1/2010 | Carter et al. | |
| 7,651,688 B2 | 1/2010 | Hanai et al. | |
| 7,666,662 B2 | 2/2010 | Sharma et al. | |
| 7,695,936 B2 | 4/2010 | Carter et al. | |
| 7,919,257 B2 | 4/2011 | Hoogenboom et al. | |
| 7,942,042 B2 | 5/2011 | Kawakita et al. | |
| 8,188,231 B2 | 5/2012 | Lazar et al. | |
| 8,216,805 B2 | 7/2012 | Carter et al. | |
| 8,227,577 B2 | 7/2012 | Klein et al. | |
| 8,242,247 B2 | 8/2012 | Klein et al. | |
| 8,268,314 B2 | 9/2012 | Baehner et al. | |
| 8,304,713 B2 | 11/2012 | Pradel | |
| 8,309,300 B2 | 11/2012 | Jununtula et al. | |
| 8,796,424 B2 | 8/2014 | Croasdale et al. | |
| 8,945,552 B2 | 2/2015 | Baehner et al. | |
| 9,150,639 B2 | 10/2015 | Yamasaki et al. | |
| 9,241,994 B2 | 1/2016 | Igawa | |
| 2002/0062010 A1 | 5/2002 | Arathoon et al. | |
| 2002/0155537 A1 | 10/2002 | Carter et al. | |
| 2003/0099974 A1 | 5/2003 | Lillie et al. | |
| 2003/0124129 A1 | 7/2003 | Oliner | |
| 2004/0018557 A1 | 1/2004 | Qu et al. | |
| 2004/0033561 A1 | 2/2004 | O'Keefe et al. | |
| 2004/0038339 A1 | 2/2004 | Kufer et al. | |
| 2004/0220388 A1 | 11/2004 | Metens et al. | |
| 2005/0064509 A1 | 4/2005 | Bradbury et al. | |
| 2005/0079170 A1 | 4/2005 | Le Gall et al. | |
| 2005/0152894 A1 | 7/2005 | Krummen et al. | |
| 2005/0163782 A1 | 7/2005 | Glaser et al. | |
| 2005/0054048 A1 | 10/2005 | Grasso et al. | |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Stevenson, Anti-Cancer Drug Design, vol. 3, p. 219-230, 1989.*
Caron, Journal of Experimental Medicine, vol. 176, p. 1191-1195, 1992.*
Chitnis, Clinical Cancer Research, vol. 14, p. 6364-6370, 2008.*
Kontermann (Biodrugs, vol. 23, No. 2, p. 93-109, 2009).*
Davis (Protein Engineering, Design & Selection, vol. 23, No. 4, p. 195-202, 2010).*
Krugman (The Journal of Immunology, vol. 159, p. 244-249, 1997).*
Tao (J. Exp. Med., vol. 173, p. 1025-1028, 1991).*
Greenwood (Eur. J. Immunology, vol. 23, p. 1098-1104, 1993).*
Pleas (The Journal of Biology Chemistry, vol. 274, No. 33, p. 23508-23514, 1999).*
Nagaoka (Protein Engineering, vol., 16, No. 4, p. 243-245, 2003).*
Schaefer, W. et al., "Immunoglobulin domain crossover as a generic approach for the production of bispecific IgG antibodies" Proceedings of the National Academy of Sciences 108(27):11187-11192 (Jul. 5, 2011).

(Continued)

*Primary Examiner* — Michael Allen
(74) *Attorney, Agent, or Firm* — Morrison & Foerster LLP

(57) ABSTRACT

The present invention relates to antigen binding proteins comprising two Fc parts, methods for their production, pharmaceutical compositions containing said antigen binding proteins, and uses thereof.

3 Claims, 15 Drawing Sheets

(56) References Cited

U.S. PATENT DOCUMENTS

| | | |
|---|---|---|
| 2005/0249722 A1 | 10/2005 | Beliard et al. |
| 2006/0063921 A1 | 3/2006 | Moulder et al. |
| 2006/0122370 A1 | 6/2006 | Oliner et al. |
| 2006/0134709 A1 | 6/2006 | Stavenhagen et al. |
| 2006/0160184 A1* | 7/2006 | Mattheus Hoogenboom et al. ..... 435/69.1 |
| 2006/0280747 A1 | 12/2006 | Fuh et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0269369 A1 | 11/2007 | Gegg et al. |
| 2007/0274985 A1 | 11/2007 | Dubel et al. |
| 2007/0274998 A1 | 11/2007 | Uktu |
| 2008/0063641 A1 | 3/2008 | Huang et al. |
| 2008/0187951 A1 | 8/2008 | Kallmeier et al. |
| 2009/0155275 A1 | 6/2009 | Wu et al. |
| 2009/0162359 A1 | 6/2009 | Klein et al. |
| 2009/0162360 A1* | 6/2009 | Klein et al. ............... 424/136.1 |
| 2009/0194692 A1 | 6/2009 | Kobaru |
| 2009/0175851 A1 | 7/2009 | Klein et al. |
| 2009/0232811 A1 | 9/2009 | Klein et al. |
| 2009/0304715 A1* | 12/2009 | Masuho et al. ............ 424/173.1 |
| 2010/0015133 A1 | 1/2010 | Igawa et al. |
| 2010/0081796 A1 | 4/2010 | Brinkman et al. |
| 2010/0111967 A1 | 5/2010 | Baehner et al. |
| 2010/0196362 A1* | 8/2010 | Stavenhagen et al. .... 424/133.1 |
| 2010/0254989 A1 | 10/2010 | Bossenmaier et al. |
| 2010/0256338 A1 | 10/2010 | Brinkmann et al. |
| 2010/0256340 A1 | 10/2010 | Brinkmann et al. |
| 2010/0286374 A1 | 11/2010 | Kannan et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0149879 A1 | 6/2012 | Brinkmann et al. |
| 2012/0164726 A1 | 6/2012 | Klein et al. |
| 2012/0225071 A1 | 6/2012 | Klein et al. |
| 2012/0177637 A1 | 7/2012 | Hoogenboom et al. |
| 2012/0184718 A1 | 7/2012 | Bruenker et al. |
| 2012/0237507 A1 | 9/2012 | Bossenmaier et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0112914 A1 | 4/2014 | Nezu et al. |
| 2014/0154254 A1 | 6/2014 | Kannan et al. |
| 2014/0199294 A1 | 7/2014 | Mimoto et al. |
| 2014/0370019 A1 | 12/2014 | Bruenker et al. |
| 2014/0370020 A1 | 12/2014 | Kuramochi |
| 2015/0344570 A1 | 12/2015 | Igawa et al. |
| 2016/0168259 A1 | 1/2016 | Igawa |
| 2016/0039937 A1 | 2/2016 | Yamasaki et al. |
| 2016/0075785 A1 | 3/2016 | Ast et al. |
| 2016/0238600 A1 | 4/2016 | Hoogenboom et al. |
| 2017/0096485 A1 | 4/2017 | Bacac et al. |
| 2017/0096495 A1 | 4/2017 | Bacac et al. |
| 2017/0114135 A1 | 4/2017 | Codarri-Deak et al. |
| 2017/0114146 A1 | 4/2017 | Klein et al. |

FOREIGN PATENT DOCUMENTS

| | | |
|---|---|---|
| CN | 12302039 A | 10/1999 |
| CN | 1603345 A | 4/2005 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 | 3/1989 |
| EP | 0 637 593 A1 | 2/1995 |
| EP | 1 870 458 A1 | 12/2007 |
| EP | 1 870 459 | 12/2007 |
| EP | 1 925 319 A1 | 5/2008 |
| EP | 2 050 764 A1 | 4/2009 |
| EP | 2 443 154 B1 | 4/2012 |
| EP | 2 554 669 A1 | 2/2013 |
| EP | 2 647 707 A1 | 10/2013 |
| EP | 2 728 002 A1 | 5/2014 |
| EP | 2 787 078 A1 | 10/2014 |
| EP | 2 940 135 A1 | 11/2015 |
| JP | 2008-531049 A | 8/2008 |
| RU | 2005/124281 A | 1/2006 |
| RU | 2295537 C2 | 3/2007 |
| WO | WO-93/06217 A1 | 4/1993 |
| WO | WO-94/09131 A1 | 4/1994 |
| WO | WO-94/10202 A1 | 5/1994 |
| WO | 94/29350 | 12/1994 |
| WO | 95/09917 | 4/1995 |
| WO | 96/27011 | 9/1996 |
| WO | WO-1996/27612 A1 | 9/1996 |
| WO | WO-97/01580 A1 | 1/1997 |
| WO | WO-97/14719 A1 | 4/1997 |
| WO | 97/028267 | 8/1997 |
| WO | WO-98/45322 A3 | 10/1998 |
| WO | WO-98/45331 A2 | 10/1998 |
| WO | WO-98/45331 A3 | 10/1998 |
| WO | WO-98/45332 A2 | 10/1998 |
| WO | WO-98/50431 A2 | 11/1998 |
| WO | 99/37791 | 7/1999 |
| WO | 99/54324 | 10/1999 |
| WO | WO-99/66951 A2 | 12/1999 |
| WO | WO-99/66951 A3 | 12/1999 |
| WO | WO-99/66951 C1 | 12/1999 |
| WO | WO-00/05265 A2 | 2/2000 |
| WO | WO-00/35956 A1 | 6/2000 |
| WO | 00/16739 | 10/2000 |
| WO | 01/77342 | 10/2001 |
| WO | WO-01/77342 A1 | 10/2001 |
| WO | WO-2001/90192 A2 | 11/2001 |
| WO | WO-02/02781 A1 | 1/2002 |
| WO | WO-02/33073 A1 | 4/2002 |
| WO | WO-02/096948 A2 | 12/2002 |
| WO | WO-03/030833 A2 | 4/2003 |
| WO | WO-03/030833 A3 | 4/2003 |
| WO | 03/035835 | 5/2003 |
| WO | WO-03/035835 A2 | 5/2003 |
| WO | WO-03/035835 A3 | 5/2003 |
| WO | 03/055993 | 7/2003 |
| WO | WO-03/057134 A2 | 7/2003 |
| WO | WO-03/057134 A3 | 7/2003 |
| WO | WO-03/097105 A1 | 11/2003 |
| WO | WO-03/106501 A1 | 12/2003 |
| WO | WO-2004/003019 A2 | 1/2004 |
| WO | WO-2004/003019 A3 | 1/2004 |
| WO | WO-2004/032961 A1 | 4/2004 |
| WO | WO-2004/058298 A1 | 7/2004 |
| WO | 2004/065540 | 8/2004 |
| WO | WO-2004/072117 A2 | 8/2004 |
| WO | WO-2004/072117 A3 | 8/2004 |
| WO | WO-2004/106375 A1 | 12/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | 2005/011735 | 2/2005 |
| WO | 2005/18572 | 3/2005 |
| WO | 2005/027966 | 3/2005 |
| WO | 2005/044859 | 5/2005 |
| WO | WO-2005/044853 A2 | 5/2005 |
| WO | WO-2005/044853 A3 | 5/2005 |
| WO | WO-2005/051422 A1 | 6/2005 |
| WO | WO-2005/063816 A2 | 7/2005 |
| WO | WO-2005/063816 A3 | 7/2005 |
| WO | WO-2005/092925 A2 | 10/2005 |
| WO | WO-2005/092925 A3 | 10/2005 |
| WO | WO-2006/020258 A2 | 2/2006 |
| WO | WO-2006/020258 A3 | 2/2006 |

(56) References Cited

FOREIGN PATENT DOCUMENTS

| WO | WO-2006/031370 A2 | 3/2006 |
| --- | --- | --- |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/091209 A2 | 8/2006 |
| WO | WO-2006/091209 A3 | 8/2006 |
| WO | WO 2006/093794 | 9/2006 |
| WO | WO-2010/108127 A1 | 9/2006 |
| WO | 2006/103100 | 10/2006 |
| WO | WO-2006/106905 A1 | 10/2006 |
| WO | WO-2006/113665 A2 | 10/2006 |
| WO | 2006/114700 | 11/2006 |
| WO | 2006/116260 | 11/2006 |
| WO | WO-2008/132352 A1 | 12/2006 |
| WO | 2007/031875 | 3/2007 |
| WO | WO-2007/031875 A2 | 3/2007 |
| WO | WO-2007/031875 A3 | 3/2007 |
| WO | WO-2007/044887 A2 | 4/2007 |
| WO | WO-2007/044887 A3 | 4/2007 |
| WO | WO 2007/048037 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/146959 A2 | 12/2007 |
| WO | WO-2007/146959 A3 | 12/2007 |
| WO | WO-2007/147901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/027236 A2 | 3/2008 |
| WO | WO-2008/027236 A3 | 3/2008 |
| WO | WO-2008/077077 A2 | 6/2008 |
| WO | WO-2008/077077 A3 | 6/2008 |
| WO | 2008/0077546 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | 2009/080251 | 7/2009 |
| WO | 2009/080254 | 7/2009 |
| WO | WO-2009/080252 A1 | 7/2009 |
| WO | WO-2009/080253 A1 | 7/2009 |
| WO | WO-2009/089094 A1 | 7/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/065882 A1 | 6/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO 2010/145792 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/118739 A1 | 9/2011 |
| WO | WO-2011/143545 A1 | 11/2011 |
| WO | WO-2012/025525 A1 | 1/2012 |
| WO | WO-2012/025530 A1 | 3/2012 |
| WO | WO-2012/058768 A1 | 5/2012 |
| WO | WO-2012/073985 A1 | 6/2012 |
| WO | 2012/116927 | 9/2012 |
| WO | WO-2012/131555 A2 | 10/2012 |
| WO | WO-2012/131555 A3 | 10/2012 |
| WO | WO-2013/002362 A1 | 1/2013 |
| WO | WO-2013/012733 A1 | 1/2013 |
| WO | WO-2013/026833 A1 | 2/2013 |
| WO | WO-2013/026835 A1 | 2/2013 |
| WO | WO-2013/065708 A1 | 5/2013 |
| WO | WO-2013/096291 A2 | 6/2013 |
| WO | WO-2013/096291 A3 | 6/2013 |
| WO | WO-2013/150043 A1 | 10/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/049003 A1 | 4/2014 |
| WO | WO-2014/081955 A1 | 5/2014 |
| WO | WO-2014/082179 A1 | 6/2014 |
| WO | WO-2014/104165 A1 | 7/2014 |
| WO | WO-2016/016299 A1 | 2/2016 |
| WO | WO-2016/055432 A2 | 4/2016 |
| WO | WO-2016/055432 A3 | 4/2016 |
| WO | WO-2017/055385 A1 | 4/2017 |
| WO | WO-2017/055392 A1 | 4/2017 |
| WO | WO-2017/055393 A1 | 4/2017 |

OTHER PUBLICATIONS

Atwell et al., "Stable heterodimers from remodeling the domain interface of a homodimer using a phage display library" J. Mol. Biol. 270(1):26-35 (1997).

Ausbel et al. Current Protocols in Molecular Biology New York, New York:Greene Publishing and Wiley Interscience, (1995).

Barnes et al., "Advanced in animal cell recombinant protein production: GS-NSO expression system" Cytotechnology 32(2):109-123 (Feb. 2000).

Barnes et al., "Characterization of the stability of recombinant protein production in the GS-NSO expression system" Biotechnol Bioeng 73(4):261-270 (May 2001).

Boerner et al., "Production of Antigen—Specific Human Monoclonal Antibodies From In Vitro-Primed Human Splenocytes" J Immunol. 147(1):86-95 (Jul. 1991).

Brüggmann et al., "Comparison of the effector funtions of human immunoglobulins using a matched set of chimeric antibodies" J Exp Med. 166(5):86-95 (Nov. 1987).

Brüggmann et al., "Designer Mice: The Production of Human Antibody Repertoires in Transgenic Animals" Year in Immuno 7:33-40 (1993).

Brunhouse et al., "Isotypes of IgG: comparison of the primary structures of three pairs of isotypes which differ in their ability to activate complement" Mol Immunol. 16(11):907-917 (Nov. 1979).

Burton et al., "The Clq Receptor Site on Immunoglobulin G" Nature 288(5789):338-344 (Nov. 27, 1980).

Carter et al., "Humanization of an Anti-p185her2 Antibody for Human Cancer Therapy" Proc Natl Acad Sci USA. 89(10):4285-4289 (May 1992).

Cohen et al., "Nonchromosomal Antibiotic Resistance in Bacteria: Genetic Transformation of *Escherichia coli* by R-Factor DNA" Proc. Natl. Acad. Sci. USA 69(8):2110-2114 (Aug. 1972).

Cole et al. Monoconal Antibodies and Cancer Therapy "The EBV-Hybridoma Technique and Its Application to Human Lung Cancer" New York, New York:Alan R. Liss, Inc., pp. 77-96 (1985).

(56) References Cited

OTHER PUBLICATIONS

Coloma et al., "Design and production of novel tetravalent bispecific antibodies" Nature Biotechnology 15(2):159-163 (Feb. 1997).
Davies et al., "Expression of GnTIII in a Recombinant Antl•CD20 CHO Production Cell L1ne: Expression of Antibodies with Altered Glycoforms Leads to an Increase in ADCC Through Higher Affinity for FcyRIII" Biotechnol. Bioeng. 74:288-294 (2001).
Durocher et al., "High-level and high-throughput recombianant protein production by transient transfection of suspension-growing human 293-EBNA1 cells" Nucleic Acids Research• 30(2e9):nine pages. (2002).
Edelman et al., "The covalent structure of an entire yG immunoglobulin molecule" Proc. Natl. Acad. Sci. USA 63:78-85 (1969).
Fischer et al., "Bispecific Antibodies: Molecules that Enable Novel Therapeutic Strategies" Pathobiology 74:3-14 (2007).
Geisse et al., "Eukaryotic Expression Systems: A comparison" Protein Expression and Purification 8:271-282 (1996).
Goldberg et al., "Bi-Specific Antibodies that Bind Specific Target Tissue and Targeted Conjugates" Derwent Information Ltd., 12 pages (2012).
Graham et al., "A new technique for the assay of infectivity of human adenovirus 5 DNA" Virology 52(2):456-467 (1973).
Hezareh et al., "Effector Function Activities of a Panel of Mutants of a Broadly Neutralizing Antibody against Human Immunodeficiency Virus Type 1" Journal of Virology 75(24):12161-12168 (Dec. 2001).
Hollinger et al., "Engineered antibody fragments and the rise of single domains" Nat Biotechnol. 23(9):1126-1136 (Sep. 2005).
Hoogenboom et al., "By-passing immunisation. Human antibodies from synthetic repertoires of germline VH gene segments rearranged in vitro" J Mol Biol. 227(2):381-388 (Sep. 20, 1992).
Idusogie et al., "Mapping of the Clq Binding Site on Rituxan, a Chimeric Antibody with a Human IgG1 Fc" The Journal of Immunology 164:4178-4184 (2000).
Jakobovits et al., "Analys1s of Homozygous Mutant Chimeric Mice: Deletion of the Immunoglobin Heavy-Chain Joining Region Blocks B-cell Development and Antibody Production" Proc. Natl. Acad. Sci. USA 90(6):2551-2555 (Mar. 15, 1993).
Jakobovits et al., "Germ-line Transmission and Expression of a Human-derived Yeast Artificial Chromosome" Nature 362:255-258 (Mar. 1993).
Jefferis et al., "YgG-Fc-mediated effector functions: molecular definition of interaction sites for effector ligands and the role of glycosylation" Immunol Rev. 163:59-76 (1998).
Johnson et al., "Kabat Database and its applications: 30 years after the first variability plot" Nucleic Acids Research 28(1):214-218 (2000).
Kabat et al. Sequences of Proteins of Immunological Interest "Table of Contents" 5th edition, Bethesda, MD:Public Health Service, vol. 1 (1991).
Kabat et al., "Evolutionary and structural influences on light chain constant (C/subL/nor) region of human and mouse immunoglobulins" Proc. Natl. Acad. Sci. USA 72(7):2785-2788 (Jul. 1975).
Kaufman et al., "Overview of Vector Design for Mammalian Gene Expression" Molecular Biotechnology 16:151-161 (2000).
Kobayshi et al., "Similarities in the Biodistribution of Iodine-Labeled Anti•Tac Single-Chain Disulfide-Stabilized Fv Fragment and Anti-Tac Disulfide-Stabilized Fv Fragment" Nuclear Medicine & Biology 25:387-393 (1998).
Lifely et al., "Glycosylation and Biological Activity of CAMPATH-1H Expressed in Different Cell Lines and Grown Under Different Culture Conditions" Glycobiology 5(8):813-822 (Dec. 1995).
Love et al., "Recombinant antibodies possessing novel effector functions" Methods in Enzymology 178:515-527 (1989).
Lukas et al., "Inhibition of C1-Mediatea Immune Hemolys1s by Monomeric arid Dimeric Peptides from the Second Constant Domain of Human Immunoglobulin G1" The Journal of Immunolgy 127(6):2555-2560 (Dec. 1981)

Lund et al., "Oligosaccharide-protein interactions in IgG can modulate recognition by Fcy receptors" FASEB Journal 9:115-119 (1995).
Makrides, "Components of Vectors for Gene Transfer and Expression in Mammalian Cells" Protein Expression and Purification 17:183-202 (1999).
Marks et al., "By-Passing Immunization: Human Antibodies From V-gene Librarles Displayed on Phage" J Mol Biol. 222(3):581-597 (Dec. 5, 1991).
Meissner et al., "Transient Gene Expression: Recombinant Protein Production with Suspension-Adapted HEK293-EBNA Cells" Biotechnology and Bioengineering 75:197-203 (2001).
Merchant et al., "An efficient route to human bispecific IgG" Nature Biotechnology 16:677-681 (1998).
Milstein et al., "Hybrid Hybridomas and Their Use in Immunohistochemistry" Nature 305:537-540 (Oct. 6, 1983).
Mimura et al., "Role of Oligosaccharide Residues of IgG1-Fc in FcyRIIb Binding" The Journal of Biological Chemistry 276(49):45539-45547 (Dec. 7, 2001).
Morgan et al., "he N-terminal End of the CH2 Domain of Chimeric Human IgG1 anti-HLA-DR is Necessary for Clq, FcyRIII Binding" Immunology 86:319-324 (1995).
Morrison et al., "Chimeric Human Antibody Molecules: Mouse Antigen-Binding Domains with Human Constant Region Domains" Proc. Natl. Acad. Sci. USA 81(21):6851-6855 (Nov. 1984).
Morrison et al., "Two Heads are Better than One" Nature Biotechnology 25(11):1233-1234 (Nov. 2007).
Morrison, "Success in Specification" Nature 368:812-813 (Apr. 1994).
Neuberger et al., "A hapten-specific chimaeric IgE antibody with human physiological effector function" Nature 314:268-270 (Mar. 21, 1985).
Niwa et al., "IgG subclass-independent improvement of antibody-dependent cellular cytotoxicity by fucose removal from Asn297-linked oligosaccharides" J. Immunol. Methods 306:151-160 (2005).
Norderhaug et al., "Versatile Vectors for Transient and Stable Expression of Recombinant Antibody Molecules in Mammalian Cells" Journal of Immunological Methods 204:77-87 (1997).
Orlandi et al., "Cloning Immunoglobulin Variable Domains for Expression by the Polymerase Chain Reaction" Proc. Natl. Acad. Sci. USA 86:3833-3837 (May 1989).
Pace et al., "How to Measure and Predict the Molar Absoption Coefficient of a Protein" Protein Science 4(11):2411-2423 (Nov. 1995).
Radaev et al., "Recognition of IgG by Fcy Receptor" The Journal of Biological Chemistry 276(19):16478-16483 (May 11, 2001).
Rajgopal et al., "A Form of Anti-Tac(Fv) Which is Both Single-chain and Disulfide Stabilized: Comparison with its single chain and Disulfide-stabilized Homologs" Protein Engineering 10(12):1453-1459 (1997).
Raju, "Iycosylation Variations with Expression Systems and Their Impact on Biological Activity of Therapeutic Immunoglobulins" BioProcess International 1(4):44-53 (Apr. 2003).
Ridgeway et al., "Knobs-into-holes' Engineering of Antibody CH3 Domains for Heavy Chain Heterdimerization" Protein Engineering 9(7):617-621 (1996).
Riechmann et al., "Reshaping Human Antibodies for Therapy" Nature 332:323-327 (Mar. 24, 1988).
Routier et al., "The Glycosylation Pattern of a Humaized IgGl Antibody (D1.3) Expressed in CHO Cells" Glycoconjugate Journal 14:201-207 (1997).
Sambrook et al. Molecular Cloning: A Laboratory Manual "Table of Contents" Cold Spring Harbor, New York:Cold Spring Harbor Laboratory Press, (1989).
Schlaeger et al., "Transient Gene Expression in Mammalian Cells Grown in Serum-free Suspension Culture" Cytotechnology 30:71-83 (1999).
Schlaeger, "The Protein Hydrolysate, Primatone RL, is a Cost Effective Multiple Growth Promoter of Mammalian Cell Culture in Serum-containing and Serum-free Media and Displays Anti apoptosis Properties" Journal of Immunological Methods 194:191-199 (1996).

(56) References Cited

OTHER PUBLICATIONS

Schmidt et al., "Suppression of Metastasis Fomation by a Recombinant Single Chain Antibody-Toxin Targeted to Full-length and Oncogenic Variant EGF Receptors" Oncogene 18:1711-1721 (1999).
Shen et al., "Single Variable Domain Antibody as a Versatile Building Block for the constructio of IgG-like Bispecific Antibodies" Journal of Immunological Methods 318:65-74 (2007).
Shields et al., "High Resolution Mapping of the Binding Site on Human IgG1 for FvγRI, FcγRII, FcγRIII and FcRn and Design of IgG1 Variants with Improved Binding to the FcγR" Journal of Biological Chemistry 276(9):6591-6604 (2001).
Shields et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).
Shinkawa et al., "The Absence of Fucose but Not the Presence of galactose or Bisecting N-Acetylglucosamine of Human IgG1 Complex-Type Oligosaccharides Shows the Critical Role of Enhancing Antibodiy-Dependent Cellular cytotoxicity" J. Biol. Chem. 278(5):3466-3473 (Jan. 31, 2003).
Simmons et al., "Expression of full-length immunoglobulins in *Escherichia coli*: Rapid and Efficient production of aglycosylated antibodies" Journal of Immunological Methods 263:133-147 (2003).
Simon et al., "Antibody Domain Mutants Demonstrate Autonomy of the Antigen Binding Site" The EMBO Journal 9(4):1051-1055 (1990).
Thommesen et al., "Lysine 322 in the Human IgG3 C/SubH/nor2 Domain is Crucial for Antibody Dependent Complement Activation" Molecular Immunology 37:995-1004 (2000).
Umana et al., "Engineered Glycoforms of an Antineuroblastoma IgG1 with Optimized Antibody-Dependent Cellular Cytotoxic Activity" Nature Biotechnology 17(2):176-180 (Feb. 1999).
Van Dijk et al., "Human antibodies as next generation therapeutics" Curr Opin Chem Biol. 5(4):368-374 (Aug. 2001).
Vigayalakshmi et al., "Antibody Purification Methods" Applied Biochemistry and Biotechnology 75:93-102 (1998).
Werner et al., "Appropriate Mammalian Expression Systems for Biopharmaceuticals" Drug Research 48(8):870-880 (1998).
Willems et al., "Optimizing Expression and Purification from Cell Culture Medium of Trispecific Recombinant Antibody Derivatives" Journal of Chromatography B 786:161-176 (2003).
Woof et al., "Human Antibody-FC Receptor Interactions Illuminated by Crystal Structures" Nat. Rev. Immunol. 4:89-99 (2004).
Wright et al., "Effect of Glycosylation on Antibody Function: Implications for Genetic Engineering" Trends in Biotechnology 15:26-32 (1997).
Wu et al., "Simultaneous Targeting of Multiple Disease Mediators by a Dual-Variable-Domain Immunoglobulin" Nature Biotechnology 25(11):1290-1297 (Nov. 2007).
Aggarwal et al., "Fibroblast Activation Protein Peptide Substrates Identified from Human Collagen I Derived Gelatin Cleavage Sites," *Biochemistry* 47(3):1076-1086, (Jan. 22, 2008).
Anonymous., "Production in yeasts of stable antibody fragments," *Expert Opinion on Therapeutic Patents* 7(2):179-183, (1997).
Avgeris et al., "Kallikrein-related peptidase genes as promising biomarkers for prognosis and monitoring of human malignancies," *Biol. Chem* 391(5):505-511, (May 2010).
Bao et al., "HER2-mediated upregulation of MMP-1 is involved in gastric cancer cell invasion," *Arch Biochem Biophys* 499(1-2):49-55, (Jul. 2010).
Bera et al., "A bivalent disulfide-stabilized Fv with improved antigen binding to erbB2," *J. Mol. Biol.* 281(3):475-483, (Aug. 21, 1998).
Boado et al., "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).

Borgström et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Briggs et al., "Cystatin E/M suppresses legumain activity and invasion of human melanoma," *BMC Cancer* 10(17):1-13, (Jan. 2010).
Brinkmann., "Disulfide-stabilized Fv fragments," Chapter 14 in Antibody Engineering, Kontermaan et al. eds., vol. 2, Springer-Verlag, Berlin Heidelberg, Germany, pp. 181-189, (Apr. 30, 2010).
Brinkmann et al., "A recombinant immunotoxin containing a disulfide-stabilized Fv fragment," *PNAS* 90(16):7538-7542, (1993).
Brorson et al., "Mutational Analysis of Avidity and Fine Specificity of Anti-Levan Antibodies," *J. Immunol.* 163:6694-6701 (1994).
Brummell et al., "Probing the combining site of an anti-carbohydrate antibody by saturation-mutagenesis: role of the heavy-chain CDR3 residues," *Biochemistry* 32(4):1180-1187 (1993).
Burgess et al., "Possible dissociation of the heparin-binding and mitogenic activities of heparin-binding (acidic fibroblast) growth factor-1 from its receptor-binding activities by site-directed mutagenesis of a single lysine residue," *Journal of Cell Biology* 111:2129-2138, (Nov. 1990).
Burks et al., "In vitro scanning saturation mutagenesis of an antibody binding pocket," *PNAS* 94(2):412-417 (1997).
Carro et al., "Serum insulin-like growth factor I regulates brain amyloid-β levels," *Nature Medicine* 8(12):1390-1397, (2002, e-pub. Nov. 4, 2002).
Carter., "Bispecific human IgG by design," *Immunol. Methods* 248:7-15, (2001).
Chan, L.A. et al., "Variable Region Domain Exchange in Human IgGs Promotes Antibody Complex Formulation with Accompanying Structural Changes and Altered Effector Functions," *Molecular Immunology* 41(5):527-538. (2004).
Chung et al., "Development of a novel albumin-binding prodrug that is cleaved by urokinase-type-plasminogen activator (uPA)," *Bioorg Med Chem Lett.* 16(19):5157-5163 (Oct. 1, 2006).
Coleman., "Effects of amino acid sequence changes on antibody-antigen interactions," *Research in Immunol.* 145(1):33-36, (1994).
Cordingley et al., "Substrate requirements of human rhinovirus 3C protease for peptide cleavage in vitro," *J. Biol. Chem.* 265(16):9062-9065, (1990).
Cortesio et al., "Calpain 2 and PTP1 B function in a novel pathway with Src to regulate invadopodia dynamics and breast cancer cell invasion," *J. Cell Biol.* 180(5):957-971, (Mar. 10, 2008).
Coxon et al., "Combined treatment of angiopoietin and VEGF pathway antagonists enhances antitumor activity in preclinical models of colon carcinoma," *99th AACR Annual Meeting*, Abstract #1113, (Apr. 2008).
Crawford et al., "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al. "Extracellular proteases as targets for drug development," *Curr. Protein Pept Sci* 10(4):297-307, (Aug. 2009).
Cullen et al., "Granzymes in cancer and immunity," *Cell Death Differ* 17(4):616-623, (Apr. 2010).
Dall'Acqua, W. et al. (1998). "Contribution of Domain Interface Residues to the Stability of Antibody CH3 Domain Homodimers", *Biochemistry*, 37:9266-9273.
Deyev., "Multivalency: the hallmark of antibodies used for optimization of tumor targeting by design," *Bioessays* 30(9):904-918, (2008).
Dimmock, N.J. et al. (2004). "Valency of antibody binding to virions and its determination by surface plasmon resonance", *Rev. Med. Virol.*, 14:123-135.
Donaldson et al., "Design and development of masked therapeutic antibodies to limit off-target effects: Application to anti-EGFR antibodies," *Cancer Biology & Therapy* 8(22):2145-2150, (Nov. 15, 2009).
Dufner et al., "Harnessing phage and ribosome display for antibody optimization," *Trends Biotechol.* 24(11):523-29 (2006).

(56) References Cited

OTHER PUBLICATIONS

Flatman et al., "Process analytics for purification of monoclonal antibodies," *J. Chromatogr B* 848:79-87, (2007).
Galamb et al., "Inflammation, adenoma and cancer: objective classification of colon biopsy specimens with gene expression signature," *Dis Markers* 25(1):1-16, (2008).
Gerspach et al., "Target-selective activation of a TNF prodrug by urokinase-type plasminogen activator (uPA) mediated proteolytic processing at the cell surface," *Cancer Immunol. Immunother* 55:1590-1600 (2006).
Gold et al., "A novel bispecific, trivalent antibody construct for targeting pancreatic carcinoma," *Cancer Res.* 68(12):4819-4826, (2008).
Grote et al., "Bispecific Antibody Derivatives Based on Full-Length IgG Formats," Chapter 16 in *Methods in Molecular Biology* 901:247-263, (2012).
Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Hartog et al., "The Insulin-like growth factor 1 receptor in cancer: Old focus, new future," European Journal of Cancer, Pergamon Press, Oxford, GB, 43(13):1895-1904, (Aug. 23, 2007).
Henry et al., "Clinical implications of fibroblast activation protein in patients with colon cancer," *Clin Cancer Res.* 13(6):1736-1741, (Mar. 15, 2007).
Hollander., "Bispecific antibodies for cancer therapy," *Immunotherapy* 1(2):211-222, (Mar. 2009).
Hust et al., "Single Chain Fab (scFab) Fragment," *BMC Biotechnology* 7(14):1-15, (Mar. 8, 2007).
Huston, J.S. et al. (1993). "Medical Applications of Single-Chain Antibodies," *Intern. Rev. Immunol.* 10(2-3):195-217.
Ibragimova et al., "Stability of the β-Sheet of the WW domain: A molecular dynamics simulation study," *Biophysical Journal* 77:2191-2198, (Oct. 1999).
International Search Report dated Dec. 6, 2011, for PCT Patent Application No. PCT/EP2011/064476 filed on Aug. 23, 2011, seven pages.
International Search Report dated Dec. 6, 2011, for PCT Patent Application No. PCT/EP2011/064468 filed on Aug. 23, 2011, seven pages.
Jang et al., "The structural basis for DNA binding by an anti-DNA autoantibody," *Mol. Immunol.* 35(18):1207-1217 (1998).
Jendreyko et al., "Simultaneous, Phenotypic Knockout of VEGF-R2 and Tie-2 With an Intradiabody Enhances Antiangiogenic Effects In Vivo," Therapieoptimierung and Risikostratifizierung, Scripps Research Institute, 218:143-151, (2006).
Jia et al., "A novel trifunctional IgG-like bispecific antibody to inhibit HIV-1 infection and enhance lysis of HIV by targeting activation of complement," *Virology Journal* 7(142):1-4, (Jun. 29, 2010).
Karadag et al., "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 2006).
Kazama et al., "Hepsin, a putative membrane-associated serine protease, activates human factor VII and initiates a pathway of blood coagulation on the cell surface leading to thrombin formation," *JBC* 270:66-72, (1995).
Kim et al., "Inhibition of Vascular Endothelial Growth Factor-Induced Angiogenesis Suppresses Tumour Growth In Vivo," *Nature* 362:841-844, (1993).
Kleinschmidt et al., "Design of a modular immunotoxin connected by polyionic adapter peptides," *J. Mol. Biol.* 327(2):445-452, (Mar. 21, 2003).
Kobayshi et al. "Tryptophan H33 plays an important role in pyrimidine (6-4) pyrimidone photoproduct binding by a high-affinity antibody," *Protein Engineering* 12(10):879-844 (1999).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Lamkanfi et al., "Inflammasomes: guardians of cytosolic sanctity," *Immunol. Rev.* 227(1):95-105, (Jan. 2009).
Lazar et al., "Transforming growth factor α: Mutation of aspartic acid 47 and leucine 48 results in different biological activities," *Molecular and Cellular Biology* 8(3):1247-1252, (Mar. 1988).
Lee et al., "Using substrate specificity of antiplasmin-cleaving enzyme for fibroblast activation protein inhibitor design," *Biochemistry* 48(23):5149-5158, (Jun. 16, 2009).
Leeman et al., "The Structure, Regulation, and Function of Human Matrix Metalloproteinase-13," *Crit. Rev Biochem Mol. Biol.* 37(3):149-166, (2002).
Liang et al., "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Lin et al., "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).
Liotta et al., "Metastatic potential correlates with enzymatic degradation of basement membrane collagen," *Nature* 284(5751) 67-68, (Mar. 6, 1980).
Liu et al., "Clinical and imaging diagnosis of primary hepatic lymphoma," *J First Mil Med. Univ*, 25(10):1290-1292, three pages, (2005). (Translation of the Abstract Only.).
Lopez-Otin et al., "The regulatory crosstalk between kinases and proteases in cancer," *Nat. Rev. Cancer* 10(4):278-292, (Apr. 2010).
Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al., "ADAMTS1 and MMP1 proteolytically engage EGF-like ligands in an osteolytic signaling cascade for bone metastasis," *Genes Dev.* 23(16):1882-1894, (Aug. 2009).
Mamoune et al., "Calpain-2 as a target for limiting prostate cancer invasion," *Cancer Res.* 63(15):4632-4640, (Aug. 2003).
Marvin et al., "Recombinant approaches to IgG-like bispecific antibodies," *Acta Pharmacol. Sin.* 26:649-658, (2005).
Marvin et al., "Bispecific antibodies for dual-modality cancer therapy: killing two signaling cascades with one stone," *Curr. Opin. Drug Discov. Devl.* 9:184-193, (2006).
Matrisian. "Cancer biology: extracellular proteinases in malignancy," *Curr. Biol.* 9(20):R776-R778, (Oct. 1999).
McLean, G.R. et al. (2005). "A point mutation in the CH3 domain of human IgG3 inhibits antibody secretion without affecting antigen specificity", *Molecular Immunology*, 42:1111-1119.
Melnyk et al., Vascular Endothelial Growth Factor Promotes Tumor Dissemination by a Mechanism Distinct from Its Effect on Primary Tumor Growth, *Cancer Research* 56:921-924, (1996).
Miller et al., "Design, Construction, and in Vitro Analyses of Multivalent Antibodies," *J. Immunol.* 170:4854-4861, (2003).
Minn et al., "Genes that Mediate Breast Cancer Metastasis to Lung," *Nature* 436(7050):518-524, (Jul. 2005).
Mirny, L. et al. (2001). "Protein Folding Theory: From Lattice to All-Atom Models", *Annu. Rev. Biophys. Biomol. Struct.*, 30-361-96.
Morrison et al., "Variable region domain exchange influences the functional properties of IgG," *Journal of Immunology, American Association of Immunologists* 160:2802-2808, (Jan. 1, 1998).
Müller et al., "The first constant domain ($C_H1$ and $C_L$) of an antibody used as heterodimerization domain for bispecific miniantibodies," *FEBS Letters* 422:259-264, (1998).
Müller et al., "Recombinant Bispecific Antibodies for Cellular Cancer Immunotherapy," *Current Opinion in Molecular Therapeutics* 9:319-326, (2007).
Müller et al., "Bispecific Antibodies," Chapter 2 in Handbook of Therapeutic Antibodies, Dübel, S. ed., Wiley-VCH Verlag GmbH & Company KGaA, Weinheim, pp. 345-378, (2007).

(56) References Cited

OTHER PUBLICATIONS

Mukhopadhyay et al., "Matrix metalloproteinase-12 is a therapeutic target for asthma in children and young adults," *J. Allergy Clin Immunol.* 126:70-76, (2010).
Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).
Novotný, J. et al. (1985). "Structural invariants of antigen binding: Comparison of immunoglobulin $V_L$-$V_H$ and $V_L$-$V_L$ domain dimmers", *Proc. Natl. Acad. Sci. USA*, 82:4592-4596.
Ohno et al., "Antigen-binding specificities of antibodies are primarily determined by seven residues of $V_H$," *Proc. Natl. Acad. Sci. USA* 82(9):2945-2949, (May 1985).
Oliner et al., Suppression of Angiogenesis and Tumor Growth by Selective Inhibition of Angiopoietin-2, *Cancer Cell* 6:507-516, (2004).
Orcutt, et al., "A modular IgG-scFv bispecific antibody topology," *Protein Engineering, Design & Selection* 23(4):221-228, (Apr. 2010, e-pub. Dec. 17, 2009).
Pakula et al., "Genetic analysis of protein stability and function," *Annu. Rev. Genet.* 23:289-310, (1989).
Plückthun et al., "New Protein Engineering Approaches to Multivalent and Bispecific Antibody Fragments," *Immunotechnology* 3:83-105, (1997).
PreScission Protease, GE Healthcare Catalogue No. 27-0843-01, located at http://www.gelifesciences.com/webapp/wcs/stores/servlet/productByld/en/GELifeScience, last visited on Jul. 10, 2013, one page.
Rawlings., "A large and accurate collection of peptidase cleavages in the MEROPS database," Database (Oxford), pp. 1-14, (2009, e-pub. Nov. 2, 2009).
Reiter et al., "Cytotoxic and antitumor activity of a recombinant immunotoxin composed of disulfide-stabilized anti-Tac Fv fragment and truncated *Pseudomonas* exotoxin," *International Journal of Cancer* 58:142-149, (1994).
Reiter et al., "Antitumor activity and pharmacokinetics in mice of a recombinant immunotoxin containing a disulfide-stabilized Fv fragment," *Cancer Research* 54:2714-2718, (1994).
Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).
Reiter et al., "Disulfide stabilization of antibody Fv: computer predictions and experimental evaluation," *Protein Engineering* 8:1323-1331, (1995).
Reiter et al., "Construction of a functional disulfide-stabilized TCR Fv indicates that antibody and TCR Fv frameworks are very similar in structure," *Immunity* 2:281-287, (1995).
Reiter et al., "Engineering antibody Fv fragments for cancer detection and therapy: disulfide-stabilized Fv fragments," *Nature Biotechnology* 14:1239-1245, (1996).
Roitt et al., "Immunology" English Translation by McElroy Translation Company, Moscow "Mir" (2000), p. 110-111, eight pages.
Roitt A. et al., (2000), "Multispecific Antibodies Comprising Full Length Antibodies and Single Chain Fab Fragments," *Immunology*, English Translation, Moscow:Mir, pp. 388-389.
Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Ruppert et al., "Protease levels in breast, ovary and other gynecological tumor tissues: prognostic importance in breast cancer," *Cancer Detect. Prev.* 21(5):452-459, (1997).
Schmiedl et al., "Expression of a bispecific dsFv-dsFv' antibody fragment in *Escherichia coli*," *Protein Engineering* 13(10):725-734, (Oct. 2000).
Schoonjans, et al., "Fab Chains as an Efficient Heterodimerization Scaffold for the Production of Recombinant Bispecific and Trispecific Antibody Derivatives," *Journal of Immunology* 165:7050-7057, (2000).
Schwartz et al., "A superactive insulin: [B10-aspartic acid]insulin(human)," *Proc. Natl. Acad. Sci. USA* 84:6408-6411, (Sep. 1987).
Scott et al., "Biologic protease inhibitors as novel therapeutic agents," *Biochimie* 92(11):1681-1688, (Nov. 2010).
Shen et al. "Single variable domain-IgG fusion: A novel recombinant approach to Fc domain-containing bispecific antibodies," J. of Biological Chemistry 281(16):10706-10714, (Apr. 21, 2006, e-pub. Feb. 15, 2006).
Singer, M. and Berg, P. "Genes and genomes," Moscoer, MIR 1(1998) 63-64 (With English Translation.).
Stetler-Stevenson et al., "Progelatinase A activation during tumor cell invasion," *Invasion Metastasis* 14(1-6):259-268, (1994-1995).
Torres, M. et al. (2005). "Variable-Region-Identical Antibodies Differing in Isotype Demonstrate Differences in Fine Specificity and Idiotype", *The Journal of Immunology*, 174:2132.
Tripathi et al., "Laminin-332 is a substrate for hepsin, a protease associated with prostate cancer progression," *JBC* 283:30576-30584, (2008).
Van Spriel et al., "Immunotherapeutic perspective for bispecific antibodies," *Immunology Today* 21(8):391-397, (Aug. 2000).
Van't Veer et al., "Gene expression profiling predicts clinical outcome of breast cancer," *Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Veveris-Lowe et al., "Seminal Fluid Characterization for Male Fertility and Prostate Cancer: Kallikrein-Related Serine Proteases and whole Proteome Approaches," *Semin Thromb Hemost.* 33(1):87-99, (2007).
Walker et al., "Efficient and Rapid Affinity Purification of Proteins Using Recombinant Fusion Proteases," *Bio/Technology* 12:601-605, (1994).
Warren et al., "Regulation of Vascular Endothelial Growth Factor of Human Colon Cancer Tumorigenesis in a Mouse Model of Experimental Liver Metastasis," *J. Clin. Invest.* 95:1789-1797, (1995).
Webber et al., "Preparation and characterization of a disulfide-stabilized Fv fragment of the anti-Tac antibody: comparison with its single-chain analog," *Molecular Immunology* 32:249-258, (1995).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Wright et al., "ADAM28: a potential oncogene involved in asbestos-related lung adenocarcinomas," *Genes Chromosomes Cancer* 49(8);688-698, (Aug. 2010).
Written Opinion of the International Searching Authority dated Dec. 6, 2011, for PCT Patent Application No. PCT/EP2011/064476 filed on Aug. 23, 2011, four pages.
Written Opinion of the International Searching Authority dated Dec. 6, 2011, for PCT Patent Application No. PCT/EP2011/064468 filed on Aug. 23, 2011, four pages.
Xie et al., "A New format of bispecific antibody: Highly efficient heterodimerization, expression and tumor cell lysis," *J. of Immunol. Methods* 296:95-101, (2005).
Zeidler et al., "Simultaneous activation of T cells and accessory cells by a new class of intact bispecific antibody results in efficient tumor cell killing," *Journal of Immunology* 163:1246-1252, (1999).
Zuo et al., "An efficient route to the production of an IgG-like bispecific antibody," *Protein Engineering* 13(5):361-367, (2000).
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.

(56) References Cited

OTHER PUBLICATIONS

Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
Taiwanese Search Report for Taiwanese Patent Application No. 099110151, filed on Apr. 1, 2010, Completion of Search Sep. 12, 2012, 1 page.
International Search Report dated Aug. 5, 2010, for PCT Application No. PCT/EP2010/003559, filed on Jun. 14, 2010, 10 pages.
Russian Office Action dated Apr. 18, 2013, for Russian Patent Application No. 2010 129 539, 3 pages.
Russian Office Action dated Oct. 8, 2014, for Russian Patent Application No. 2012 100 865, 3 pages.
Bird et al. "Single-Chain Antigen-Binding Proteins," *Science* 242(4877):423-6, (Oct. 21, 1988).
Bird et al. "Single-Chain Antigen-Binding Proteins," Science 244(4903):409, *Erratum*, (Apr. 28, 1989).
Bostrom et al. (2009). "Variants of the antibody herceptin that interact with HER2 and VEGF at the antigen binding site," *Science* 323:1610-1614.
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.
Castoldi et al. (2012). "Molecular characterization of novel trispecific ErbB-cMet-IGF1R antibodies and their antigen-binding properties," *Prot. Engin. Des. Selection* 25:551-560.
Chernaia, "[Cathepsin L from human brain tumor. Purification and contents]." Ukr Biokhim Zh. 70(5):97-103, (Sep.-Oct. 1998). (English Translation of Abstract.) (Article in Russian).
Cuesta et al. (2010). "Multivalent antibodies: when design surpasses evolution," *Trends Biotech*. 28:355-362.
Fenn, S. et al., "Crystal Structure of an Anti-Ang2 CrossFab Demonstrates Complete Structural and Functional Integrity of the Variable Domain" *Plos One* 8(4):e61953 (Apr. 1, 2013).
Huston et al. "Protein engineering of antibody binding sites: recovery of specific activity in an anti-digoxin single-chain Fv analogue produced in *Escherichia coli,*" *Proc. Natl. Acad. Sci. U.S.A.* 85(16):5879-5883, (Aug. 1988).
International Search Report dated Jul. 29, 2013, for PCT Patent Application No. PCT/EP2013/060529, filed on May 22, 2013, seven pages.
Johnson et al. "Construction of single-chain Fv derivatives monoclonal antibodies and their production in *Escherichia coli,*" *Methods Enzymol*. 203:88-98, (1991).
Klein, C. et al., "Progress in overcoming the chain association issue in bispecific heterodimeric IgG antibodies" mAbs 4(6):653-663 ( 2012).
Metz et al. (2012). "Bispecific antibody derivatives with restricted binding functionalities that are activated by proteolytic processing," *Prot. Engin. Des. Selection* 25:571-580.
Pan, Q. et al. "Blocking Neuropilin-1 Function Has an Additive Effect with nti-VEGF to Ihibit Tumor Growth," *Cancer Cell* 11:53-67, (Jan. 2007).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al. "Improved binding and antitumor activity of a recombinant anti-erbB2 immunotoxin by disulfide stabilization of the Fv fragment," *JBC* 269:18327-18331, (1994).
Reiter et al. "Engineering interchain disulfide bonds into conserved framework regions of Fv fragments: improved biochemical characteristics of recombinant immunotoxins containing disulfide-stabilized Fv," *Protein Eng*. 7(5):697-704, (May 1994).
Stork et al. "A novel tri-functional antibody fusion protein with improved pharmacokinetic properties generated by fusing a bispecific single-chain diabody with an albumin-binding domain from streptococcal protein G," *Protein Eng. Des. Sel*. 20(11):569-576, (Nov. 2007, e-pub. Nov. 3, 2007).
Written Opinion of the International Searching Authority dated Jul. 29, 2013, for PCT Patent Application No. PCT/EP2013/060529, filed on May 22, 2013, seven pages.
Baserga et al. (2003). "The IGF-1 Receptor in Cancer Biology," *Int. J. Cancer* 107:873-877.
Myatt et al. "Pathogenic Potential of Human Monoclonal Immunoglobulin Light Chains: Relationship of in vitro Aggregation to in vivo Organ Deposition," *Proc. Natl. Acad. Sci. USA* 91:3034-3038, (Apr. 1994).
Ueki et al. "Expression of Hepatocyte Growth Factor and its Receptor c-met Proto-Oncogene in Hepatocellular Carcinoma," *Hepatology* 25(4):862-866, (1997).
Wallash et al. (1995). "Heregulin-Dependent Regulation of HER2/neu Oncogenic Signaling by Heterodimerization With HER3," *EMBO J*. 14(17):4267-4275.
U.S. Appl. No. 14/551,957, filed on Nov. 24, 2014 for Castoldi et al.
Berkman, R.A. et al. "Expression of the Vascular Permeability Factor/Vascular Endothelial Growth Factor Gene in Central Nervous System Neoplasms," *J. Clin. Invest*. 91:153-159, (Jan. 1993).
Brown, L.F. et al. "Expression of Vascular Permeability Factor (Vascular Endothelial Growth Factor) and its Receptors in Breast Cancer," *Human Pathol*. 26(1):86-91, (Jan. 1995).
Brown, L.F. et al. "Expression of Vascular Permeability Factor (Vascular Endothelial Growth Factor) and its Receptors in Adenocarcinomas of the Gastrointestinal Tract," *Cancer Res*. 53:4727-4735, (Oct. 1, 1993).
Cheung, A.H. et al. "Endothelial Tie2/Tek Ligands Angiopoietin-1 (*ANGPT1*) and Angiopoietin-2 (*ANGPT2*): Regional Localization of the Human Genes to 8q22.3-q23 and 8p23," *Genomics* 48(3):389-391, (Mar. 15, 1998).
Connolly, D.T. et al. "Human Vascular Permeability Factor," *J. Biol. Chem*. 264(33):20017-20024, (Nov. 25, 1989).
Dvorak, H. et al. "Vascular Permeability Factor/Vascular Endothelial Growth Factor, Microvascular Hyperpermeability, and Angiogenesis," *Am. J. Pathol*. 146(5):1029-1039, (May 1995).
Ferrara, N. et al. "The Biology of Vascular Endothelial Growth Factor," *Endocr. Rev*. 18(1):4-25, (1997).
International Search Report, dated Sep. 29, 2015 for PCT/EP2015/067369, filed on Jul. 29, 2015, 3 pages.
Keck, P.J. et al. "Vascular Permeability Factor, An Endothelial Cell Mitogen Related to PDGF," *Science* 246:1309-1312, (1989).
Kim, I. et al. "Molecular Cloning and Characterization of a Novel Angiopoietin Family Protein, Angiopoietin-3," *FEBS Let*. 443:353-56, (1999).
Kim, I. et al. "Molecular Cloning, Expression, and Characterization of Angiopoietin-Related Protein. Angiopoietin-Related Protein Induces Endothelial Cell Sprouting," *J. Biol. Chem*. 274(37):26523-26528, (Sep. 1999).
Leung, D.W. et al. "Vascular Endothelial Growth Factor is a Secreted Angiogenic Mitogen," *Science* 246:1306-1309, (Dec. 8, 1989).
Lewis, M.L. et al. "Generation of Bispecific IgG Antibodies by Structure-Based Design on an Orthogonal Fab Interface," *Nature Biotechnology* 32(2):191-198, (Feb. 1, 2014).
Maisonpierre, P.C. et al. "Angiopoietin-2, a Natural Antagonist for Tie2 that Disrupts in vivo Angiogenesis," *Science* 277:55-60, (Jul. 4, 1997).
Mattern, J. et al. "Association of Vascular Endothelial Growth Factor Expression With Intratumoral Microvessel Density and Tumour Cell Proliferation in Human Epidermoid Lung Carcinoma," *Brit. J. Cancer* 73:931-934, (1996).
Reyes, a.E. et al. "Pharmacokinetics of a Novel One-Armed Antibody to C-Met in Mice, Rats and Monkeys," Genentech, Inc., *Amer. Assn. Pharm. Sci*. 10:S1, (2008).

(56) References Cited

OTHER PUBLICATIONS

Surati, M. et al. "Role of MetMAb (OA-5D5) in c-MET Active Lung Malignancies," *Expert Opin. Biol. Ther.* 11(12):1655-1662, (2011).
Yancopoulos, G.D. et al. "Vascular-Specific Growth Factors and Blood Vessel Formation," *Nature* 407:242-248, (Sep. 14, 2000).
Patentee's Submission of Jun. 11, 2012, for European U.S. Pat. No. 1 957 533, filed on Oct. 23, 2006, Reply to Communication Pursuant to Article 94(3) EPC dated Dec. 2, 2011, 7 pages.
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
Beckman et al. "Antibody Constructs in Cancer Therapy. Protein Engineering Strategies to Improve Exposure in Solid Tumors," *Cancer* 109(2):170-179, (Jan. 15, 2007, e-pub. Dec. 11, 2006).
Brocks et al. "A TNF Receptor Antagonistic scFv, Which is Not Secreted in Mammalian Cells, is Expressed as a Soluble Mono- and Bivalent scFv Derivative in Insect Cells," *Immunotechnology* 3:173-184, (1997).
Casset et al. "A Peptide Mimetic of an Anti-CD4 Monoclonal," *Biochem and Biophys Res Comm.* 307:198-205, (2003).
Céspedes et al. "Mouse Models in Oncogenesis and Cancer Therapy," *Clin. Transl. Oncol.* 8(5):318-329, (2006).
Chicheportiche et al. "TWEAK, a New Secreted Ligand in the Tumor Necrosis Factor Family That Weakly Induces Apoptosis," *J. Biol. Chem.* 272(51):32401-32410, (1997).
Dennis. "Off by a Whisker," *Nature* 442:739-741, (2006).
Fiedler and Skerra. "Purification and Characterisation of His-Tagged Antibody Fragments," Chapter 17 in *Antibody Engineering*, Kontermann and Dubel (Eds.), Springer Lab Manuals, pp. 243-256, (2001).
Fujimori et al. "A Modeling Analysis of Monoclonal Antibody Percolation Through Tumors: A Binding-Site Barrier," *J. Nuc. Med.* 31(7):1191-1198, (Jul. 1990).
Hellings et al. "Interleukin-17 Orchestrates the Granulocyte Influx Into Airways After Allergen Inhalation in a Mouse Model of Allergic Asthma" *Am. J. Respir. Cell Mol. Biol.* 28:42-50, (2003).
Jackman et al. "Development of a Two-part Strategy to Identify a Therapeutic Human Bispecific Antibody That Inhibits IgE Receptor Signaling," *The Journal of Biological Chemistry* 285(27):20850-20859, (Jul. 2, 2010).
Komiyama et al. "IL-17 Plays an Important Role in the Development of Experimental Autoimmune Encephalomyelitis" *J Immunol* 177:566-573, (2006).
Kotake et al. "IL-17 in Synovial Fluids From Patients With Rheumatoid Arthritis Is a Potent Stimulator of Osteoclastogenesis,"*J. Clin. Invest.* 103:1345-1352, (1999).
Kumar et al. "Molecular Cloning and Expression of the Fabs of Human Autoantibodies in *Escherichia coli*," *J. Biol. Chem.* 275(45):35129-35136, (Nov. 10, 2000).
Leitzgen et al. "Assembly of Immunoglobulin Light Chains as a Prerequisite for Secretion," *Journal of Biological Chemistry* 272(5):3117-3123, (Jan. 31, 1997).
Lodish et al. "Post-Translational Modifications and Quality Control in the Rough ER," Chapter 17, Section 17.6 in *Molecular Cell Biology*, 4th edition, W.H. Freeman and Company, New York, pp. 707-712, (1999).
Lynch et al. "TWEAK Induces Angiogenesis and Proliferation of Endothelial Cells," *J. Biol. Chem.* 274(13):8455-8459, (Mar. 26, 1999).
Marsters et al. "Identification of a Ligand for the Death-Domain-Containing Receptor Apo3," *Curr. Biol.* 8(9):525-528, (1998).
Matusevicius et al. "Interleukin-17 mRNA Expression in Blood and CSF Mononuclear Cells is Augmented in Multiple Sclerosis," *Multiple Sclerosis* 5:101-104, (1999).
Paul. "Immunoglobulins: Structure and Function," in Fundamental Immunolgy, Jeske, D.D. et al.New York, New York, Raven Press, p. 131-165. (1 page translation of 7.9.1 Disculfide Bonds), (1984).
Rudikoff et al. "Single Amino Acid Substitution Altering Antigen-Binding Specificity," *Proc. Natl. Acad. Sci. USA* 79:1979-1983, (Mar. 1982).
Rudnick et al. "Affinity and Avidity in Antibody-Based Tumor Targeting," *Cancer Biotherapy & Radiopharmaceuticals* 24(2):155-161, (2009).
Schlatter et al. "On the Optimal Ratio of Heavy to Light Chain Genes for Efficient Recombinant Antibody Production by CHO Cells," *Biotechnol. Prog.* 21:122-133, (2005).
Schmiedl et al. "Effects of Unpaired Cysteines on Yield, Solubility and Activity of Different Recombinant Antibody Constructs Expressed in *E. coli*" *Journal of Immunological Methods* 242:101-114, (2000).
Smith-Gill et al. "Contributions of Immunoglobulin Heavy and Light Chains to Antibody Specificity for Lysozyme and Two Haptens," *J. Immunol.* 139(12):4135-4144, (Dec. 15, 1987).
Song et al. "Light Chain of Natural Antibody Plays a Dominant Role in Protein Antigen Binding," *Biochem. Biophys. Res. Comm.* 268(2):390-394, (Feb. 16, 2000).
Talmadge et al. "Murine Models to Evaluate Novel and Conventional Therapeutic Strategies for Cancer," *Am. J. Pathol.* 170(3):793-804, (Mar. 2007).
Terpe. "Overview of Tag Protein Fusions: From Molecular and Biochemical Fundamentals to Commercial Systems," *Appl Microbiol Biotechnol* 60:523-533, (2003; E-Pub. Nov. 7, 2002).
Thurber et al. "Antibody Tumor Penetration: Transport Opposed by Systemic and Antigen-Mediated Clearance," Adv. Drug Deliv. Rev. 60(12):1421-1434, (Sep. 2008, E-Pub. Apr. 24, 2008).
Voskoglou-Nomikos et al. "Clinical Predictive Value of the in Vitro Cell Line, Human Xenograft, and Mouse Allograft Preclinical Cancer Models," *Clin. Can. Res.* 9:4227-4239, (Sep. 15, 2003).
Ward et al. "Binding Activities of a Repertoire of Single Immunoglobulin Variable Domains Secreted From *Escherichia coli*," Nature 341:544-546, (Oct. 12, 1989).
Ziolkowska et al. "High Levels of IL-17 in Rheumatoid Arthritis Patients: IL-15 Triggers In Vitro IL-17 Production Via Cyclosporin A-Sensitive Mechanism," *J. Immunol.* 164:2832-2838, (2000).
International Search Report dated Sep. 9, 2015, for PCT Application No. PCT/EP2015/057165, filed on Apr. 1, 2015, 5 pages.
Written Opinion dated Sep. 9, 2015, for PCT Application No. PCT/EP2015/057165, filed on Apr. 1, 2015, 7 pages.
U.S. Appl. No. 15/281,484, filed Sep. 30, 2016, for Bacac et al.
U.S. Appl. No. 15/281,493, filed Sep. 30, 2016, for Bacac et al.

\* cited by examiner

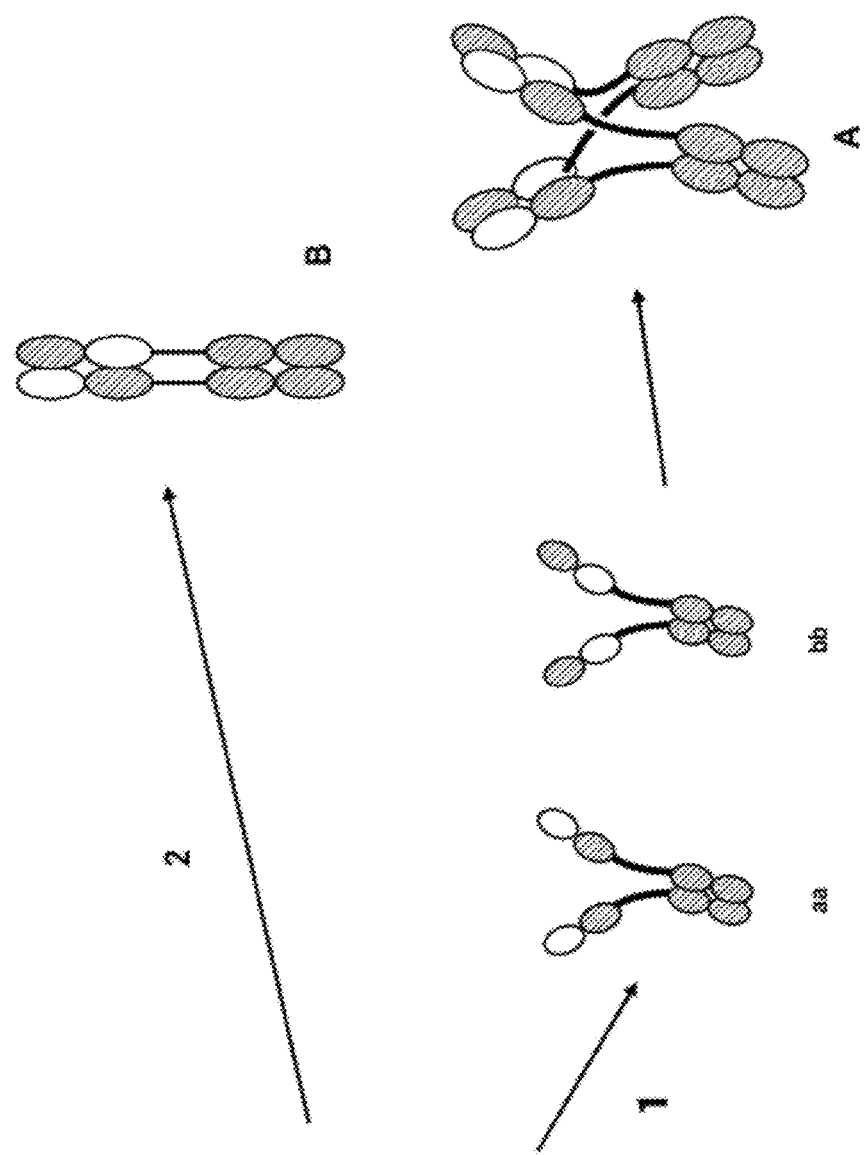
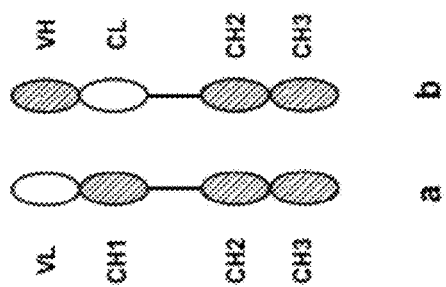
Fig. 1C

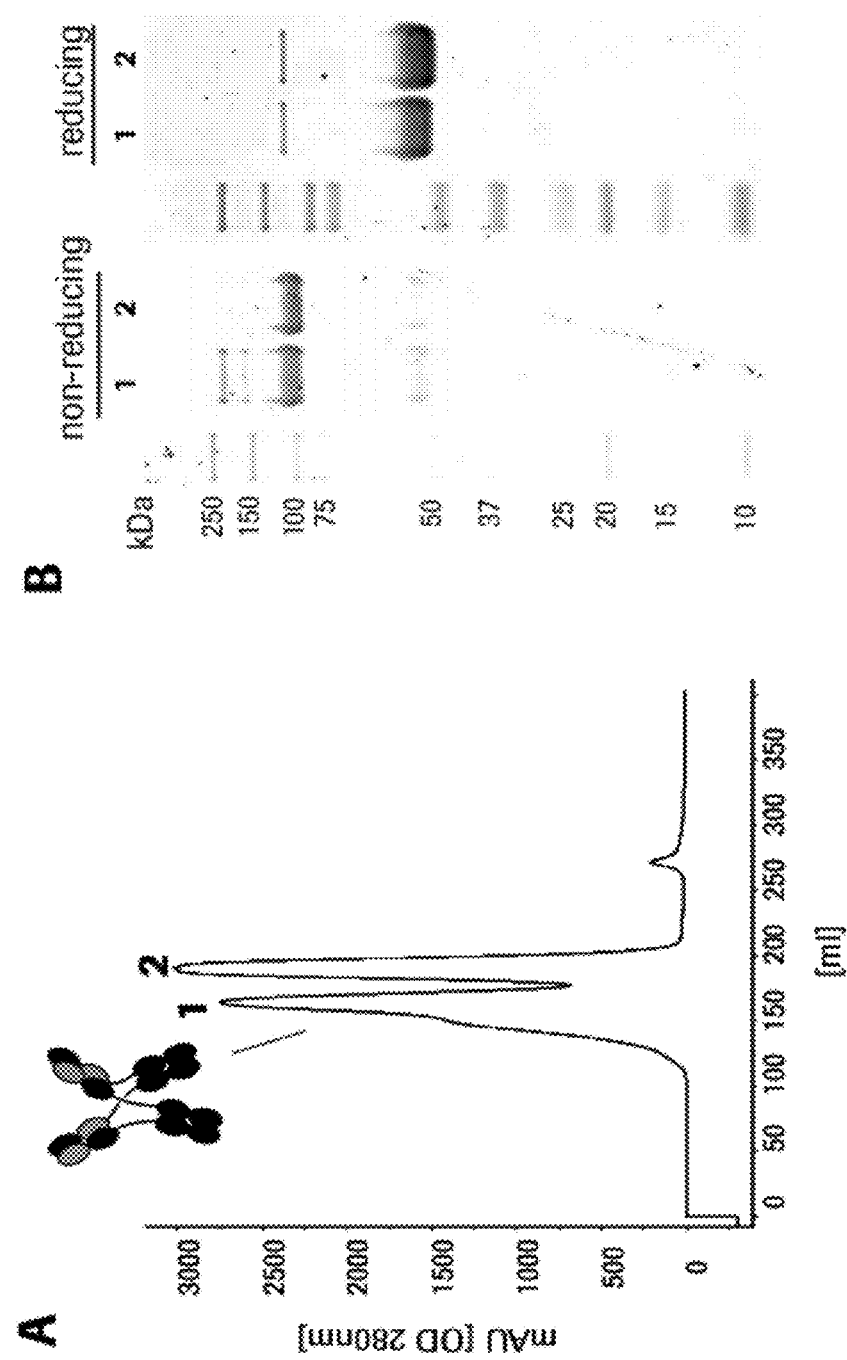
Fig. 3A and B

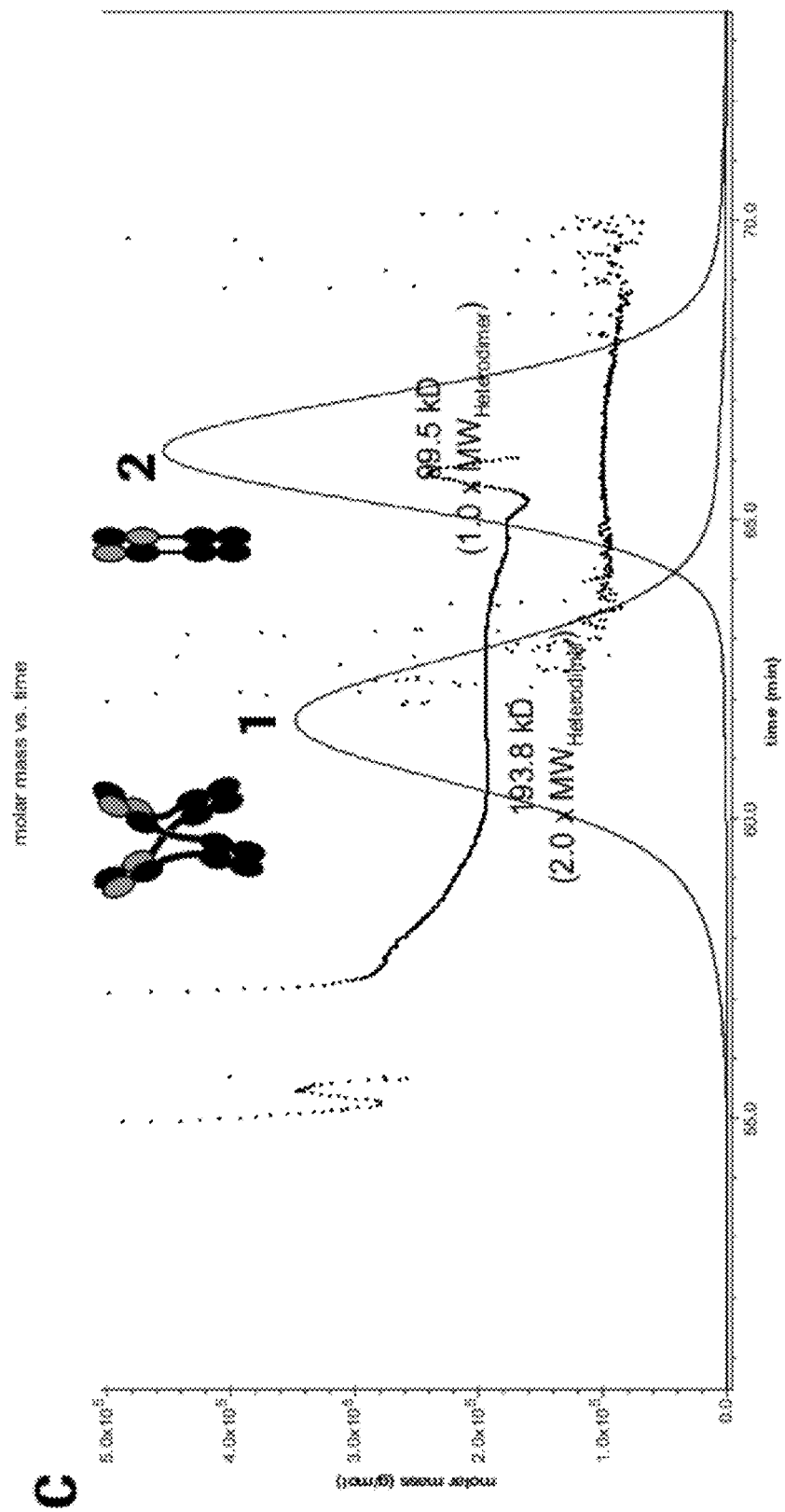

Fig. 4
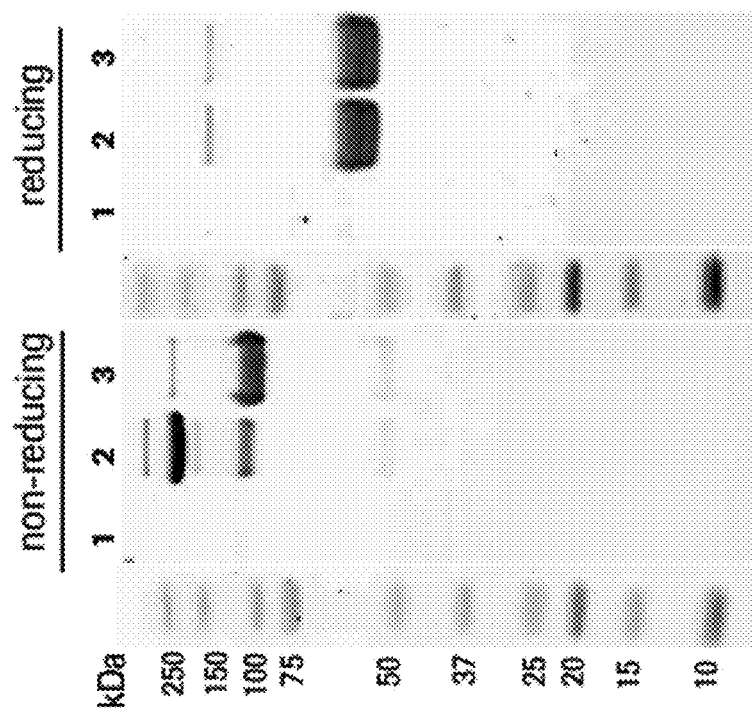
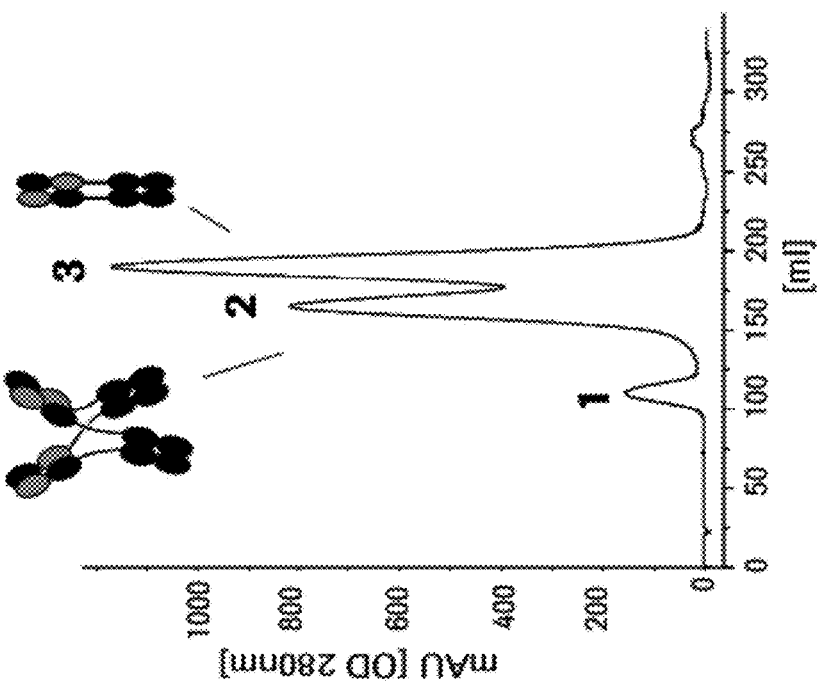

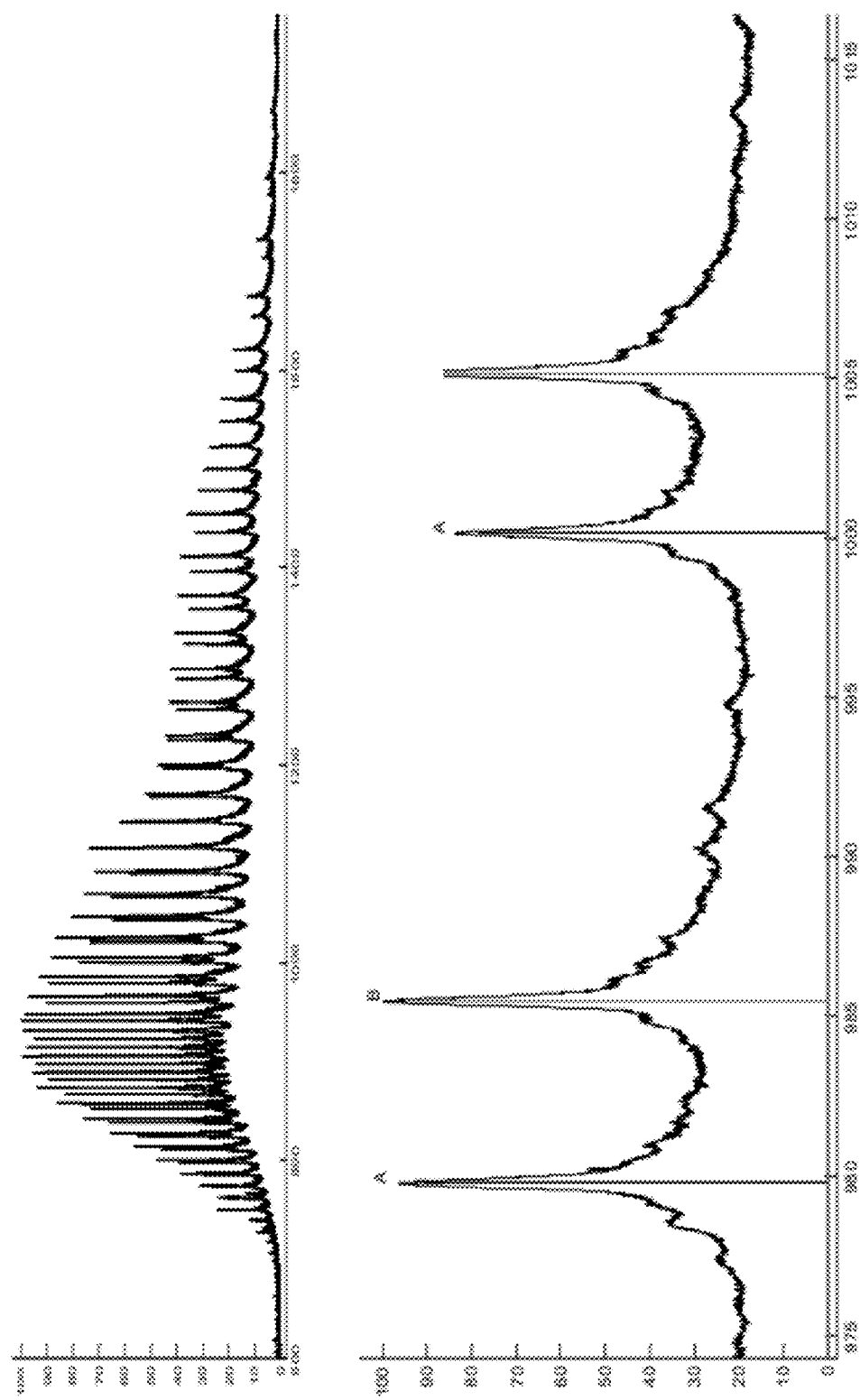

SEQUENCE LISTING

<160> NUMBER OF SEQ ID NOS: 9

<210> SEQ ID NO 1
<211> LENGTH: 445
<212> TYPE: PRT
<213> ORGANISM: Artificial Sequence
<220> FEATURE:
<223> OTHER INFORMATION: Description of Artificial Sequence: Synthetic
c-Met 5D5 MoAb-Dimer ("CH3-wt") - modified heavy
chain a) VL-CH1-CH2-CH3 polypeptide

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic
      c-Met 5D5 MoAb-Dimer ("CH3-wt") - modified heavy
      chain b) VH-CL-CH2-CH3 polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
            35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Val Ala Ala Pro Ser Val Phe
            115                 120                 125

Ile Phe Pro Pro Ser Asp Glu Gln Leu Lys Ser Gly Thr Ala Ser Val
            130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
            165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
            210                 215                 220
```

```
Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 3
<211> LENGTH: 440
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer ("CH3-wt") - modified heavy
      chain a) VL-CH1-CH2-CH3 polypeptide

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
```

```
                115                 120                 125
    Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                    165                 170                 175

Ser Val Val Thr Val Pro Ser Ser Leu Gly Thr Gln Thr Tyr Ile
                180                 185                 190

Cys Asn Val Asn His Lys Pro Ser Asn Thr Lys Val Asp Lys Lys Val
                195                 200                 205

Glu Pro Lys Ser Cys Asp Lys Thr His Thr Cys Pro Pro Cys Pro Ala
        210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                    245                 250                 255

Val Asp Val Ser His Glu Asp Pro Glu Val Lys Phe Asn Trp Tyr Val
                260                 265                 270

Asp Gly Val Glu Val His Asn Ala Lys Thr Lys Pro Arg Glu Glu Gln
                275                 280                 285

Tyr Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                    325                 330                 335

Arg Glu Pro Gln Val Tyr Thr Leu Pro Pro Ser Arg Asp Glu Leu Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                    405                 410                 415

Ser Cys Ser Val Met His Glu Ala Leu His Asn His Tyr Thr Gln Lys
                420                 425                 430

Ser Leu Ser Leu Ser Pro Gly Lys
            435                 440

<210> SEQ ID NO 4
<211> LENGTH: 452
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer ("CH3-wt") - modified heavy
      chain b) VH-CL-CH2-CH3 polypeptide

<400> SEQUENCE: 4

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30
```

-continued

```
Gly Met His Trp Val Arg Gln Ala Pro Gly Lys Gly Leu Glu Trp Val
        35                  40                  45
Ala Ile Ile Trp Phe Asp Gly Ser Ser Thr Tyr Tyr Ala Asp Ser Val
 50                  55                  60
Arg Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Phe Cys
                 85                  90                  95
Ala Arg Glu Leu Gly Arg Arg Tyr Phe Asp Leu Trp Gly Arg Gly Thr
                100                 105                 110
Leu Val Ser Val Ser Ser Ala Ser Val Ala Ala Pro Ser Val Phe Ile
            115                 120                 125
Phe Pro Pro Ser Asp Glu Gln Leu Lys Ser Gly Thr Ala Ser Val Val
130                 135                 140
Cys Leu Leu Asn Asn Phe Tyr Pro Arg Glu Ala Lys Val Gln Trp Lys
145                 150                 155                 160
Val Asp Asn Ala Leu Gln Ser Gly Asn Ser Gln Glu Ser Val Thr Glu
                165                 170                 175
Gln Asp Ser Lys Asp Ser Thr Tyr Ser Leu Ser Ser Thr Leu Thr Leu
            180                 185                 190
Ser Lys Ala Asp Tyr Glu Lys His Lys Val Tyr Ala Cys Glu Val Thr
        195                 200                 205
His Gln Gly Leu Ser Ser Pro Val Thr Lys Ser Phe Asn Arg Gly Glu
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
```

Ser Pro Gly Lys
    450

<210> SEQ ID NO 5
<211> LENGTH: 445
<212> TYPE: PRT
<213> ORGANISM: Artificial Sequence
<220> FEATURE:
<223> OTHER INFORMATION: Description of Artificial Sequence: Synthetic
      Her3 205 MoAb-Dimer ("CH3-wt") - modified heavy
      chain a) VL-CH1-CH2-CH3 polypeptide

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser

```
            340                 345                 350
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Description of Artificial Sequence: Synthetic
      Her3 205 MoAb-Dimer ("CH3-wt") - modified heavy
      chain b) VH-CL-CH2-CH3 polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 7
<211> LENGTH: 446
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer - modified heavy chain
      a) VL-CH1-CH2-CH3 with IgA-CH3 domain polypeptide

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140
```

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys Asp Lys Thr His Thr Cys Pro Pro Cys Pro Ala
        210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Asn Thr
                325                 330                 335

Phe Arg Pro Glu Val His Leu Leu Pro Pro Ser Glu Glu Leu Ala
                340                 345                 350

Leu Asn Glu Leu Val Thr Leu Thr Cys Leu Ala Arg Gly Phe Ser Pro
                355                 360                 365

Lys Asp Val Leu Val Arg Trp Leu Gln Gly Ser Gln Glu Leu Pro Arg
370                 375                 380

Glu Lys Tyr Leu Thr Trp Ala Ser Arg Gln Glu Pro Ser Gln Gly Thr
385                 390                 395                 400

Thr Thr Phe Ala Val Thr Ser Ile Leu Arg Val Ala Ala Glu Asp Trp
                405                 410                 415

Lys Lys Gly Asp Thr Phe Ser Cys Met Val Gly His Glu Ala Leu Pro
                420                 425                 430

Leu Ala Phe Thr Gln Lys Thr Ile Asp Arg Leu Ala Gly Lys
                435                 440                 445

<210> SEQ ID NO 8
<211> LENGTH: 458
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer - modified heavy chain
      b) VH-CL-CH2-CH3 with IgA-CH3 domain polypeptide

<400> SEQUENCE: 8

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val

```
                  50                  55                  60
Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
            115                 120                 125

Phe Pro Pro Ser Asp Glu Gln Leu Lys Ser Gly Thr Ala Ser Val Val
130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
            195                 200                 205

His Gln Gly Leu Ser Ser Pro Val Thr Lys Ser Phe Asn Arg Gly Glu
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Asn Thr Phe Arg Pro Glu
            340                 345                 350

Val His Leu Leu Pro Pro Ser Glu Glu Leu Ala Leu Asn Glu Leu
            355                 360                 365

Val Thr Leu Thr Cys Leu Ala Arg Gly Phe Ser Pro Lys Asp Val Leu
        370                 375                 380

Val Arg Trp Leu Gln Gly Ser Gln Glu Leu Pro Arg Glu Lys Tyr Leu
385                 390                 395                 400

Thr Trp Ala Ser Arg Gln Glu Pro Ser Gln Gly Thr Thr Thr Phe Ala
                405                 410                 415

Val Thr Ser Ile Leu Arg Val Ala Ala Glu Asp Trp Lys Lys Gly Asp
            420                 425                 430

Thr Phe Ser Cys Met Val Gly His Glu Ala Leu Pro Leu Ala Phe Thr
            435                 440                 445

Gln Lys Thr Ile Asp Arg Leu Ala Gly Lys
        450                 455

<210> SEQ ID NO 9
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 9

His His His His His
1               5
```

DUAL FC ANTIGEN BINDING PROTEINS

CROSS-REFERENCE TO RELATED APPLICATIONS

The present application claims of priority under 35 USC § 119(a) to European patent application number EP11156320.1, filed 28 Feb. 2011, the contents of which is incorporated herein by reference.

Sequence Listing

A sequence listing comprising SEQ ID NOS: 1-9 is attached hereto. Each sequence provided in the sequence listing is incorporated herein by reference, in its entirety, for all purposes. The Sequence Listing which has been submitted in ASCII format via EFS-Web was created on May 25, 2012, is named P4640-US.txt and is 33,069 bytes in size.

TECHNICAL FIELD

The present invention relates to antigen binding proteins comprising two Fc parts, methods for their production, pharmaceutical compositions containing said antigen binding proteins, and uses thereof.

BACKGROUND OF THE INVENTION

In the last two decades various engineered antibody derivatives, either mono or- multispecific, either mono- or multivalent have been developed and evaluated (see e.g. Holliger, P., et al., Nature Biotech. 23 (2005) 1126-1136; Fischer, N., and Léger O., Pathobiology 74 (2007) 3-14).

US 2004/0033561 refers to the DNA and the production of monovalent monobodies by co-expression of a heavy chain and a modified heavy chain. However during expression a considerably amount of undesired homodimer is formed as by-product, which is difficult to separate from the desired heterodimeric monobodies, as the homodimer and the heterodimer have the same or similar molecular weights. WO 2007/048037 refers to monovalent IgGs which corresponds to the heterodimeric monobodies of US 2004/0033561, but which can have a tagging moiety attached to the heavy chain for easier purification of the heterodimer from the difficult-to-separate homodimeric by-product.

SUMMARY OF THE INVENTION

The invention comprises an antigen binding protein comprising
  a) two modified heavy chains of an antibody which specifically binds to an antigen, wherein VH of each heavy chain is replaced by the VL of said antibody, said modified heavy chains being associated with each other via their CH domains of the Fc part;
  b) two modified heavy chains of said antibody wherein CH1 of each heavy chain is replaced by CL of said antibody, said modified heavy chains being associated with each other via their CH domains of the Fc part;
  and wherein the VL domains of the heavy chains of a) are associated with the VH domains of the heavy chains of b), and the CH1 domains of the heavy chains of a) are associated with the CL domains of the heavy chains of b).

In one embodiment the antigen binding protein according to the invention is characterized in that
  the CH3 domains of the Fc part of the modified heavy chains of a) and the CH3 domains of the Fc part of the modified heavy chains of b) are of the same isotype.

In one embodiment the antigen binding protein according to the invention is characterized in that
  the CH2 and CH3 domains of the Fc part of the modified heavy chains of a) and the CH2 and CH3 domains of the Fc part of the modified heavy chains of b) are of the same isotype.

In one embodiment the antigen binding protein according to the invention is characterized in that
  the CH2 and CH3 domains of the Fc part of the modified heavy chains of a) and the CH2 and CH3 domains of the Fc part of the modified heavy chains of b) are of the IgG isotype.

In one embodiment the antigen binding protein according to the invention is characterized in that
  the CH2 and CH3 domains of the Fc part of the modified heavy chains of a) and the CH2 and CH3 domains of the Fc part of the modified heavy chains of b) are of the IgG1 isotype.

In one embodiment the antigen binding protein according to the invention is characterized in comprising
  a) two modified heavy chains comprising the amino acid sequence of SEQ ID NO:1; and
  b) two modified heavy chains comprising the amino acid sequence of SEQ ID NO:2;
  a) two modified heavy chains comprising the amino acid sequence of SEQ ID NO:3; and
  b) two modified heavy chains comprising the amino acid sequence of SEQ ID NO:4; or
  a) two modified heavy chains comprising the amino acid sequence of SEQ ID NO:5; and
  b) two modified heavy chains comprising the amino acid sequence of SEQ ID NO:6.

In one embodiment the antigen binding protein according to the invention is characterized in that
  either the two modified heavy chains of a),
  or the two modified heavy chains of b),
  are further modified by the amino acid substitutions S364G, L368F, D399K and K409D (wherein the amino acid positions are numbered according to the EU Index of Kabat).

In one embodiment the antigen binding protein according to the invention is characterized in that
  a) two modified heavy chains comprising the amino acid sequence of SEQ ID NO:1; and
  b) two modified heavy chains comprising the amino acid sequence of SEQ ID NO:2;
  wherein either the two modified heavy chains of a),
  or the two modified heavy chains of b),
  are further modified by the amino acid substitutions S364G, L368F, D399K and K409D (wherein the amino acid positions are numbered according to the EU Index of Kabat);
  a) two modified heavy chains comprising the amino acid sequence of SEQ ID NO:3; and
  b) two modified heavy chains comprising the amino acid sequence of SEQ ID NO:4;

wherein either the two modified heavy chains of a),
or the two modified heavy chains of b),
are further modified by the amino acid substitutions S364G, L368F, D399K and K409D (wherein the amino acid positions are numbered according to the EU Index of Kabat);
or
a) two modified heavy chains comprising the amino acid sequence of SEQ ID NO:5; and b) two modified heavy chains comprising the amino acid sequence of SEQ ID NO:6
wherein either the two modified heavy chains of a),
or the two modified heavy chains of b),
are further modified by the amino acid substitutions S364G, L368F, D399K and K409D (wherein the amino acid positions are numbered according to the EU Index of Kabat).

In one embodiment the antigen binding protein according to the invention is characterized in that
the CH3 domains of the Fc part of the modified heavy chains of a) and
the CH3 domains of the Fc part of the modified heavy chains of b) are of a different isotype.

In one embodiment the antigen binding protein according to the invention is characterized in that
the CH3 domains of the Fc part of the modified heavy chains of a) are of the IgG1 isotype;
and the CH3 domains of the Fc part of the modified heavy chains of b) are of the IgA isotype.

In one embodiment the antigen binding protein according to the invention is characterized in comprising
a) two modified heavy chains comprising the amino acid sequence of SEQ ID NO:7; and
b) two modified heavy chains comprising the amino acid sequence of SEQ ID NO:4.

In one embodiment the antigen binding protein according to the invention is characterized in comprising
a) two modified heavy chains comprising the amino acid sequence of SEQ ID NO:3; and
b) two modified heavy chains comprising the amino acid sequence of SEQ ID NO:8.

In one embodiment the antigen binding protein according to the invention is characterized in that
The CH2 and CH3 domains of the Fc part of the modified heavy chains of a) are of the IgG1 isotype;
and the CH2 and CH3 domains of the Fc part of the modified heavy chains of b) are of the IgA isotype.

In one embodiment the antigen binding protein according to the invention is characterized in that the CH2 domain of the Fc parts of a) and b) are of IgG1 isotype, and the antigen binding protein is afucosylated with an amount of fucose of 80% or less (preferably of 65% to 5%) of the total amount of oligosaccharides (sugars) at Asn297 is of human IgG1 isotype.

The invention further comprises a method for the preparation of an antigen binding protein according to the invention
comprising the steps of
a) transforming a host cell with vectors comprising nucleic acid molecules encoding an antigen binding protein according to the invention
b) culturing the host cell under conditions that allow synthesis of said antigen binding protein molecule; and
c) recovering said antigen binding protein molecule from said culture.

The invention further comprises nucleic acid encoding the antigen binding protein according to the invention.

The invention further comprises vectors comprising nucleic acid encoding the antigen binding protein according to the invention.

The invention further comprises host cell comprising said vectors.

The invention further comprises composition, preferably a pharmaceutical or a diagnostic composition of an antigen binding protein according to the invention.

The invention further comprises pharmaceutical composition comprising an antigen binding protein according to the invention.

The invention further comprises method for the treatment of a patient in need of therapy, characterized by administering to the patient a therapeutically effective amount of an antigen binding protein according to the invention.

It has now been found that the antigen binding proteins according to the invention have valuable characteristics such as biological or pharmacological activities (as e.g. enhanced ADCC compared to parent antibodies). They can be used e.g. for the treatment of diseases such as cancer. The antigen binding proteins according to the invention have furthermore highly valuable pharmacokinetic properties (like e.g. AUC0-inf, Cmax or C0).

DESCRIPTION OF THE FIGURES

FIG. 3: Biochemical characterization of MoAb-Dimer IGF-IR (IGF-IR AK18 MoAb-Dimer ("CH3-wt")) (CH3-wt refers to the unchanged, wild type CH3 domain). (A) Protein A purified antibody was separated on an SUPERDEX® 200 26/60 column. (B) Peak fractions (1,2) were pooled and subjected to SDS-PAGE under non-reducing and reducing conditions. Polyacrylamide gels were stained with Coomassie Blue dye. Individual peaks correspond to MoAb (2) and MoAb-Dimer (1). C) The molecular mass of the peaks fractions 1 and 2 was investigated by SEC-MALLS.

FIG. 4: Biochemical characterization of Her3 205 MoAb-Dimer ("CH3-wt") (CH3-wt refers to the unchanged, wild type CH3 domain). (A) Protein A purified antibody was separated on an Superdex 200 26/60 column. (B) Peak fractions (1,2) were pooled and subjected to SDS-PAGE under non-reducing and reducing conditions. Polyacrylamide gels were stained with Coomassie Blue dye. Individual peaks correspond to MoAb (3), MoAb-Dimer (2) and a higher molecular weight aggregate (1).

FIG. 12: ESI-MS spectrum of the IGF-1R MoAb Dimer (SEC fraction 1) after degylcosylation and reduction.

DETAILED DESCRIPTION OF THE INVENTION

Figure 1A:
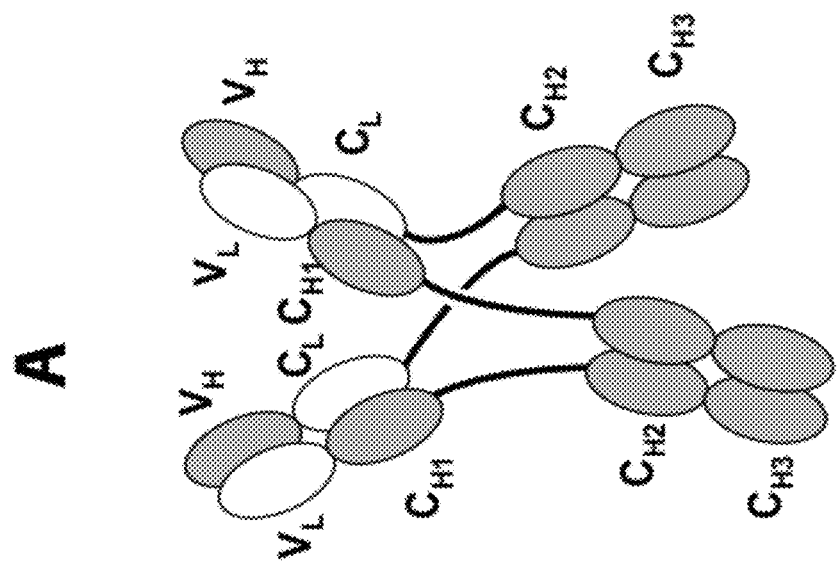
FIGS. 1A and B: A) Schematic structure of the antigen binding protein according to the invention (abbreviated MoAb-Dimer) with CH1-CL crossover. B) Scheme of the major byproduct-monovalent antibody monomer (MoAb) with CH1-CL crossover (abbreviated MoAb).

The invention comprises an antigen binding protein comprising
a) two modified heavy chains of an antibody which specifically binds to an antigen, wherein VH of each heavy chain is replaced by the VL of said antibody, said modified heavy chains being associated with each other via their CH domains of the Fc part;
b) two modified heavy chains of said antibody wherein CH1 of each heavy chain is replaced by CL of said antibody, said modified heavy chains being associated with each other via their CH domains of the Fc part;
and wherein the VL domains of the heavy chains of a) are associated with the VH domains of the heavy chains of b), and the CH1 domains of the heavy chains of a) are associated with the CL domains of the heavy chains of b).

In one embodiment the antigen binding protein according to the invention is characterized in that
the CH3 domains of the Fc part of the modified heavy chains of a) and the CH3 domains of the Fc part of the modified heavy chains of b) are of the same isotype.

In one embodiment the antigen binding protein according to the invention is characterized in that
the CH2 and CH3 domains of the Fc part of the modified heavy chains of a) and the CH2 and CH3 domains of the Fc part of the modified heavy chains of b) are of the same isotype.

In one embodiment the antigen binding protein according to the invention is characterized in that
the CH2 and CH3 domains of the Fc part of the modified heavy chains of a) and the CH2 and CH3 domains of the Fc part of the modified heavy chains of b) are of the IgG isotype.

In one embodiment the antigen binding protein according to the invention is characterized in that
the CH2 and CH3 domains of the Fc part of the modified heavy chains of a) and the CH2 and CH3 domains of the Fc part of the modified heavy chains of b) are of the IgG1 isotype.

In one embodiment the antigen binding protein according to the invention is characterized in comprising
a) two modified heavy chains comprising the amino acid sequence of SEQ ID NO:1; and
b) two modified heavy chains comprising the amino acid sequence of SEQ ID NO:2;
a) two modified heavy chains comprising the amino acid sequence of SEQ ID NO:3; and
b) two modified heavy chains comprising the amino acid sequence of SEQ ID NO:4; or
a) two modified heavy chains comprising the amino acid sequence of SEQ ID NO:5; and
b) two modified heavy chains comprising the amino acid sequence of SEQ ID NO:6.

To improve the yields of the antigen binding protein according to the invention (i.e. to improve MoAb dimer over MoAb monomer ratio (see Example 9)), the IgG1 CH3 domains of a) can be modified further by mutations so that the IgG1 CH3 domains of a) and the natural (wt) IgG1 CH3 domains of b) differ. The modification/mutation has to be carried out in a way to maintain attractive interactions between identical chains but lead to repulsion of different chains (see also FIG. 1C).

In one embodiment the antigen binding protein according to the invention is characterized in that
either the two modified heavy chains of a),
or the two modified heavy chains of b),
are further modified by the amino acid substitutions S364G, L368F, D399K and K409D (wherein the amino acid positions are numbered according to the EU Index of Kabat).

The EU Index numbering system of Kabat is described in Kabat, et al., Sequences of Proteins of Immunological Interest, 5th ed., Public Health Service, National Institutes of Health, Bethesda, Md. (1991).

In one embodiment the antigen binding protein according to the invention is characterized in that
  a) two modified heavy chains comprising the amino acid sequence of SEQ ID NO:1; and
  b) two modified heavy chains comprising the amino acid sequence of SEQ ID NO:2;
  wherein either the two modified heavy chains of a), or the two modified heavy chains of b),
  are further modified by the amino acid substitutions S364G, L368F, D399K and K409D (wherein the amino acid positions are numbered according to the EU Index of Kabat);
  a) two modified heavy chains comprising the amino acid sequence of SEQ ID NO:3; and
  b) two modified heavy chains comprising the amino acid sequence of SEQ ID NO:4;
  wherein either the two modified heavy chains of a), or the two modified heavy chains of b),
  are further modified by the amino acid substitutions S364G, L368F, D399K and K409D (wherein the amino acid positions are numbered according to the EU Index of Kabat);
  or
  a) two modified heavy chains comprising the amino acid sequence of SEQ ID NO:5; and
  b) two modified heavy chains comprising the amino acid sequence of SEQ ID NO:6
  wherein either the two modified heavy chains of a), or the two modified heavy chains of b),
  are further modified by the amino acid substitutions S364G, L368F, D399K and K409D (wherein the amino acid positions are numbered according to the EU Index of Kabat).

Another possibility to improve the yields of the antigen binding protein according to the invention (i.e. to improve MoAb dimer over MoAb monomer ratio (see Example 9)), the CH3 domains of a) and b) are taken from different isotypes. Thus the attractive interactions between identical chains are maintained but different chains are repulsed (see also FIG. 1C).

Therefore in one embodiment the antigen binding protein according to the invention is characterized in that
  the CH3 domains of the Fc part of the modified heavy chains of a) and the CH3 domains of the Fc part of the modified heavy chains of b) are of a different isotype.

In one embodiment the antigen binding protein according to the invention is characterized in that
  the CH3 domains of the Fc part of the modified heavy chains of a) are of the IgG isotype;
  and the CH3 domains of the Fc part of the modified heavy chains of b) are of the IgA isotype.

In one embodiment the antigen binding protein according to the invention is characterized in comprising
  a) two modified heavy chains comprising the amino acid sequence of SEQ ID NO:7; and
  b) two modified heavy chains comprising the amino acid sequence of SEQ ID NO:4.

In one embodiment the antigen binding protein according to the invention is characterized in comprising
  a) two modified heavy chains comprising the amino acid sequence of SEQ ID NO:3; and
  b) two modified heavy chains comprising the amino acid sequence of SEQ ID NO:8.

In one embodiment the antigen binding protein according to the invention is characterized in that
  The CH2 and CH3 domains of the Fc part of the modified heavy chains of a) are of the IgG1 isotype; and the CH2 and CH3 domains of the Fc part of the modified heavy chains of b) are of the IgA1 isotype.

In one embodiment the antigen binding protein according to the invention is characterized in that in that the CH2 domain of the Fc parts of a) and b) are of IgG1 isotype, and the antigen binding protein is afucosylated with an amount of fucose of 80% or less of the total amount of oligosaccharides (sugars) at Asn297 is of human IgG1 isotype.

The term "antibody" as used herein denotes a full length antibody consisting of two antibody heavy chains and two antibody light chains (see FIG. 1). A heavy chain of full length antibody is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the class IgE. Preferably the heavy chain of full length antibody is a polypeptide consisting in N-terminal to C-terminal direction of VH, CH1, HR, CH2 and CH3. The light chain of full length antibody is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The antibody chains are linked together via inter-polypeptide disulfide bonds between the CL domain and the CH1 domain (i.e. between the light and heavy chain) and between the hinge regions of the full length antibody heavy chains. Examples of typical full length antibodies are natural antibodies like IgG (e.g. IgG 1 and IgG2), IgM, IgA, IgD, and IgE.) The antibodies according to the invention can be from a single species e.g. human, or they can be chimerized or humanized antibodies. The full length antibodies according to the invention comprise two antigen binding sites each formed by a pair of VH and VL, which both specifically bind to the same (first) antigen.

From these full length antibodies the antigen binding protein of the invention is derived by:
  a) modifying two heavy chains of an antibody which specifically binds to an antigen, by replacing the VH domain of each heavy chain by the VL domain of said antibody;
  b) modifying two heavy chains of said antibody by replacing the CH1 domain of each heavy chain by the CL domain of said antibody.

The "Fc part" of an antibody or antigen binding protein is not involved directly in binding of an antibody to an antigen, but is responsible a) for the association of the (modified) antibody chains with each other (e.g. via their CH3 domains) and b) for various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively.

There are five types of mammalian antibody heavy chains denoted by the Greek letters: α, δ, ε, γ, and μ (Janeway, C. A., Jr. et al., Immunobiology, 5th ed., Garland Publishing (2001)). The type of heavy chain present defines the class of antibody; these chains are found in IgA, IgD, IgE, IgG, and IgM antibodies, respectively (Rhoades, R. A., and Pflanzer, R. G., Human Physiology, 4th ed., Thomson Learning (2002)). Distinct heavy chains differ in size and composition; α and γ contain approximately 450 amino acids, while μ and ε have approximately 550 amino acids.

Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof, J., and Burton, D., Nat. Rev. Immunol. 4 (2004) 89-99); heavy chains μ and ε have a constant region composed of four constant domains CH1, CH2, CH3, and CH4 (Janeway, C.A., Jr. et al., Immunobiology., 5th ed., Garland Publishing (2001)). The variable region of the heavy chain differs in antibodies produced by different B cells, but is the same for all antibodies produced by a single B cell or B cell clone. The variable region of each heavy chain is approximately 110 amino acids long and is composed of a single antibody domain.

The "CH domains of the Fc part" are the antibody heavy chain constant domain 2 (CH2), and the antibody heavy chain constant domain 3 (CH3), and optionally the antibody heavy chain constant domain 4 (CH4) in case of an antibody of the class IgE.

Figure 1B:
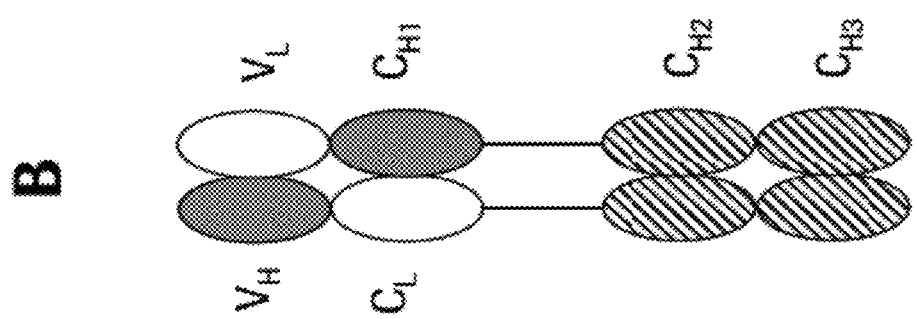
FIG. 1C: C) Association of two modified heavy chains a and b: Heterodimerisation of two different chains (a with b) directly leads to the monovalent antibody B (route 2). Homodimerisation of two identical chains (a with a and b with b) leads to the putative intermediates aa and bb (via route 1) that can associate to form "MoAb-Dimer" A. Modification of the CH3-CH3 contacts may affect distribution of products A (MoAb-Dimer) and B (MoAb). Modifications that favor heterodimerisation (e.g. knobs into holes) will increase the relative amount of compound B via route 2, whereas modifications that maintain attractive interactions between identical chains but lead to repulsion of different chains (e.g. CH3 domains of a and b taken from different isotypes) will favor route 1 and thus increase the amount of A. White: light chain domains. Dashed: heavy chain domains.

The term "said modified heavy chains being associated with each other via their CH domains of the Fc part" refers to the interchain domain pairing of the antibody heavy chain constant domains (CH) of the two modified heavy chains with each other e.g. the two CH3 domains of both chains with each other via e.g. interchain ionic interaction, Van-Der Waals interaction, or hydrogen bonding (see FIG. 1A). In one embodiment said modified heavy chains are associated with each other via at least their CH3 domains of the Fc part (and optionally via their CH2 domains, or optionally via their CH2 domains and CH4 domains (if present)).

The term "wherein the VL domains of the heavy chains of a) are associated with the VH domains of the heavy chains of b), and the CH1 domains of the heavy chains of a) are associated with the CL domains of the heavy chains of b)" refers to the domain pairing of said antibody domains (always one of a) and one of b)) as found e.g. in natural antibodies (VL/VH and CH1/CL) e.g. via interchain ionic interaction, Van-Der Waals interaction, hydrogen bonding, or disulfide interaction. (see FIG. 1A).

The "antigen binding protein" according to the invention comprises two antigen-binding sites and is bivalent. The terms "binding site" or "antigen-binding site" as used herein denotes the region(s) of antigen binding protein according to the invention to which a ligand (e.g. the antigen or antigen fragment of it) actually binds and which is derived from antibody molecule or a fragment thereof (e.g. a Fab fragment). The antigen-binding site according to the invention comprise an antibody heavy chain variable domains (VH) and an antibody light chain variable domains (VL).

The antigen-binding sites (i.e. the pairs of VH/VL) that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of a antigen binding protein of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. Bispecific antibodies are antibodies which have two different antigen-binding specificities. The antigen binding proteins according to the invention are at least monospecific and specifically bind to an epitope of the respective antigen.

The term "valent" as used within the current application denotes the presence of a specified number of binding sites in an antibody molecule. A natural antibody for example has two binding sites and is bivalent. Also the antigen binding protein according to the invention is at least bivalent.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202, 238 and No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the antigen binding protein to an epitope of the antigen in an in vitro assay, preferably in an plasmon resonance assay (BIACORE®, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity (KD) of $10^{-8}$ mol/l or less (e.g. $10^{-8}$ M to $10^{-13}$ mol/l), preferably $10^{-9}$ M to $10^{-13}$ mol/l. Thus, a antigen binding protein according to the invention is specifically binding to each antigen for which it is specific with a binding affinity ($K_D$) of $10^{-8}$ mol/l or less (e.g. $10^{-8}$ M to $10^{-13}$ mol/l), preferably $10^{-9}$ M to $10^{-13}$ mol/l.

Binding of the antigen binding protein to the FcγRIII can be investigated by a BIACORE® assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to a antigen binding proteins. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by a antigen binding protein.

In certain embodiments, an antibody is said to specifically bind an antigen when it preferentially recognizes its target antigen in a complex mixture of proteins and/or macromolecules.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes (also named isotypes): IgA, IgD, IgE, IgG and IgM, and several of these may be further divided into subclasses (also named isotypes), such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the isotypes IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and L235E and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Bunkhouse, R. and Cobra, J. J., Mol. Immunol. 16 (1979) 907-917; Burton, D. R., et al., Nature 288 (1980) 338-344; Thomason, J. E., et al., Mol. Immunol. 37 (2000) 995-1004; Idiocies, E. E., et al., J. Immunol. 164 (2000) 4178-4184; Hearer, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat which is described in Kabat, et al., Sequences of Proteins of Immunological Interest, 5th ed., Public Health Service, National Institutes of Health, Bethesda, Md. (1991)).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

Surprisingly it has been found that an antigen binding protein according to the invention shows enhanced ADCC properties compared to its parent full length antibody, especially in the area of higher antibody concentrations. These improved ADCC effects are achieved without further modification of the Fc part like glycoengineering.

Thus in one embodiment the antigen binding proteins according to the invention have an enhanced ADCC (measured as described in Example 4) compared to its parent full length antibody.

In mammals there are only two types of light chain, which are called lambda (λ) and kappa (κ). A light chain has two successive domains: one constant domain CL and one variable domain VL. The approximate length of a light chain is 211 to 217 amino acids. Preferably the light chain is a kappa (κ) light chain, and the constant domain CL is preferably derived from a kappa (κ) light chain (the constant domain Cκ).

Cell-mediated effector functions of monoclonal antibodies can be e.g. further enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M., R., et al., Glycobiology 5 (1995) 813-822; Jefferis, R., et al., Immunol. Rev. 163 (1998) 59-76; Wright, A., and Morrison, S., L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R., L., et al., J. Biol. Chem. 276 (2001) 6591-6604; Shields, R., L., et al., J. Biol. Chem. 277 (2002) 26733-26740; Simmons, L., C., et al., J. Immunol. Methods 263 (2002) 133-147).

In one aspect of the invention the antigen binding protein according to the invention is characterized in that the CH2 domains of the Fc parts of a) and b) are of IgG1 isotype, and the antigen binding protein is afucosylated with an amount of fucose of 80% or less of the total amount of oligosaccharides (sugars) at Asn297.

In one embodiment antigen binding protein is afucosylated with and the amount of fucose of 65% to 5% of the total amount of oligosaccharides (sugars) at Asn297.

The term "afucosylated antigen binding protein" refers to an antigen binding proteins of IgG1 or IgG3 isotype (preferably of IgG1 isotype) with an altered pattern of glycosylation in the Fc region at Asn297 having a reduced level of fucose residues. Glycosylation of human IgG1 or IgG3 occurs at Asn297 as core fucosylated bianntennary complex oligosaccharide glycosylation terminated with up to 2 Gal residues. These structures are designated as G0, G1 (α1,6 or α1,3) or G2 glycan residues, depending from the amount of terminal Gal residues (Raju, T. S., BioProcess Int. 1 (2003) 44-53). CHO type glycosylation of antibody Fc parts is e.g. described by Routier, F. H., Glycoconjugate J. 14 (1997)

201-207. Antibodies which are recombinantely expressed in non glycomodified CHO host cells usually are fucosylated at Asn297 in an amount of at least 85%. It should be understood that the term "antigen binding protein" as used herein includes an antigen binding protein having no fucose in its glycosylation pattern. It is commonly known that typical glycosylated residue position in an antibody is the asparagine at position 297 according to the EU numbering system ("Asn297").

Thus an afucosylated antigen binding protein according to the invention means an antigen binding protein of IgG1 or IgG3 isotype (preferably of IgG1 isotype) wherein the amount of fucose is 80% or less (e.g. of 80% to 1%) of the total amount of oligosaccharides (sugars) at Asn297 (which means that at least 20% or more of the oligosaccharides of the Fc region at Asn297 are afucosylated). In one embodiment the amount of fucose is 65% or less (e.g. of 65% to 1%), in one embodiment from 65% to 5%, in one embodiment from 40% to 20% of the oligosaccharides of the Fc region at Asn297. According to the invention "amount of fucose" means the amount of said oligosaccharide (fucose) within the oligosaccharide (sugar) chain at Asn297, related to the sum of all oligosaccharides (sugars) attached to Asn 297 (e.g. complex, hybrid and high mannose structures) measured by MALDI-TOF mass spectrometry and calculated as average value (for a detailed procedure to determine the amount of fucose, see e.g. WO 2008/077546). Furthermore in one embodiment, the oligosaccharides of the Fc region are bisected. The afucosylated antigen binding protein according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antigen binding protein fucosylation can be predetermined e.g. either by fermentation conditions (e.g. fermentation time) or by combination of at least two antigen binding protein with different fucosylation amount. Such methods to generate afucosylated antigen binding proteins are described in WO 2005/044859, WO 2004/065540, WO 2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antigen binding proteins according to the invention have an increased ADCC (compared to the parent antigen binding proteins). Other glyco-engineering methods yielding afucosylated antigen binding proteins according to the invention are described e.g. in Niwa, R. et al., J. Immunol. Methods 306 (2005) 151-160; Shinkawa, T., et al., J. Biol. Chem., 278 (2003) 3466-3473; WO 03/055993 or US 2005/0249722.

Thus one aspect of the invention is an afucosylated antigen binding protein according to the invention which is of IgG1 isotype or IgG3 isotype (preferably of IgG1 isotype) with an amount of fucose of 60% or less (e.g. of 60% to 1%) of the total amount of oligosaccharides (sugars) at Asn297.

Thus one aspect of the invention is an afucosylated antigen binding protein according to the invention which is of IgG1 isotype or IgG3 isotype (preferably of IgG1 isotype) with an amount of fucose of 60% or less (e.g. of 60% to 1%) of the total amount of oligosaccharides (sugars) at Asn297 for the treatment of cancer.

Another aspect of the invention is the use of invention an afucosylated antigen binding protein according to the invention which is of IgG1 or IgG3 isotype (preferably of IgG1 isotype) with an amount of fucose of 60% or less of the total amount of oligosaccharides (sugars) at Asn297, for the manufacture of a medicament for the treatment of cancer.

In one embodiment the amount of fucose is between 60% and 20% of the total amount of oligosaccharides (sugars) at Asn297. In one embodiment the amount of fucose is between 60% and 40% of the total amount of oligosaccharides (sugars) at Asn297. In one embodiment the amount of fucose is between 0% of the total amount of oligosaccharides (sugars) at Asn297.

The "EU numbering system" or "EU index" is generally used when referring to a residue in an immunoglobulin heavy chain constant region (e.g., the EU index reported in Kabat et al., Sequences of Proteins of Immunological Interest, 5th ed., Public Health Service, National Institutes of Health, Bethesda, Md. (1991) expressly incorporated herein by reference).

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, MD. (1991), and by Brueggemann, M., et al., J. Exp. Med. 166 (1987) 1351-1361; Love, T., W., et al., Methods Enzymol. 178 (1989) 515-527. These structures are designated as G0, G1 (α-1,6- or α-1,3-), or G2 glycan residues, depending from the amount of terminal Gal residues (Raju, T., S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis). General methods for recombinant production of antibodies are well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antigen binding proteins according to the invention are suitably separated from the culture medium by conventional immunoglobulin purification procedures such as, for example, protein A SEPHAROSE® (crosslinked beaded form of agarose), hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the antigen binding protein are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antigen binding proteins is performed in order to eliminate cellular components or other contaminants, e.g. other cellular nucleic acids or proteins (e.g. byproducts of FIG. 1B), by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102). One example of a purification is described in Example 1 and the corresponding Figures.

One aspect of the invention is a pharmaceutical composition comprising an antigen binding protein according to the invention. Another aspect of the invention is the use of an antigen binding protein according to the invention for the manufacture of a pharmaceutical composition. A further aspect of the invention is a method for the manufacture of a pharmaceutical composition comprising an antigen binding protein according to the invention. In another aspect, the present invention provides a composition, e.g. a pharmaceutical composition, containing an antigen binding protein according to the present invention, formulated together with a pharmaceutical carrier.

One embodiment of the invention is the antigen binding protein according to the invention for the treatment of cancer.

Another aspect of the invention is said pharmaceutical composition for the treatment of cancer.

One embodiment of the invention is the antigen binding protein according to the invention for use in the treatment of cancer.

Another aspect of the invention is the use of an antigen binding protein according to the invention for the manufacture of a medicament for the treatment of cancer.

Another aspect of the invention is method of treatment of patient suffering from cancer by administering an antigen binding protein according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A pharmaceutical composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al., PNAS 69 (1972) 7110).

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Amino Acid Sequences

SEQ ID NO:1 c-Met 5D5 MoAb-Dimer ("CH3-wt")—modified heavy chain a) VL-CH1-CH2-CH3

SEQ ID NO:2 c-Met 5D5 MoAb-Dimer ("CH3-wt")—modified heavy chain b) VH-CL-CH2-CH3

SEQ ID NO:3 IGF1R AK18 MoAb-Dimer ("CH3-wt")—modified heavy chain a) VL-CH1-CH2-CH3

SEQ ID NO:4 IGF1R AK18 MoAb-Dimer ("CH3-wt")—modified heavy chain b) VH-CL-CH2-CH3

SEQ ID NO:5 Her3 205 MoAb-Dimer ("CH3-wt")—modified heavy chain a) VL-CH1-CH2-CH3

SEQ ID NO:6 Her3 205 MoAb-Dimer ("CH3-wt")—modified heavy chain b) VH-CL-CH2-CH3

SEQ ID NO:7 IGF1R AK18 MoAb-Dimer—modified heavy chain a) VL-CH1-CH2-CH3 with IgA-CH3

SEQ ID NO:8 IGF1R AK18 MoAb-Dimer—modified heavy chain b) VH-CL-CH2-CH3 with IgA-CH3 domain

EXAMPLES

The present invention is described in further detain in the following examples which are not in any way intended to limit the scope of the invention as claimed. All references cited are herein specifically incorporated by reference for all that is described therein. The following examples are offered to illustrate, but not to limit the claimed invention.

Experimental Procedure

A. Materials and Methods

Recombinant DNA Techniques

Standard methods were used to manipulate DNA as described in Sambrook, J., et al., Molecular cloning: A laboratory manual; Cold Spring Harbor Laboratory Press, Cold Spring Harbor, N.Y. (1989). The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of subcloned gene fragments was confirmed by DNA sequencing. DNA sequences encoding for the two antibody chains (VH-CL-CH2-CH3 and VL-CH1-CH2-CH3) were prepared as whole fragments by gene synthesis with flanking 5'HpaI and 3'NaeI restriction sites. Gene segments coding for point mutations in the CH3 domain which preferentially lead to the MoAb-Dimer product as well as the replacement of gene segments coding for IgG1 part with an IgA-CH3 domain (e.g. SEQ. ID. NO: 7) were prepared by gene synthesis. These segments were flanked by unique restriction sites which allowed for replacement of the corresponding wild type IgG1 sequences. All constructs were designed with a 5'-end DNA sequence coding for a leader peptide, which targets proteins for secretion in eukaryotic cells.

Construction of the Expression Plasmids

A Roche expression vector was used for the construction of all antibody chains. The vector is composed of the following elements:

an origin of replication, oriP, of Epstein-Barr virus (EBV),
an origin of replication from the vector pUC18 which allows replication of this plasmid in *E. coli*
a beta-lactamase gene which confers ampicillin resistance in *E. coli*,
the immediate early enhancer and promoter from the human cytomegalovirus (HCMV),
the human 1-immunoglobulin polyadenylation ("poly A") signal sequence, and
unique HpaI, BclI, and NaeI restriction sites.

The immunoglobulin genes in the order of VH-CL-CH2-CH3 and VL-CH1-CH2-CH3 as well as constructs modified in the 3' region coding for the C-terminus of the antibody chain (CH3) were prepared by gene synthesis and cloned into pGA18 (ampR) plasmids as described. The pG18 (ampR) plasmids carrying the synthesized DNA segments and the Roche expression vector were digested either with HpaI and NaeI or with BclI and NaeI restriction enzymes (Roche Molecular Biochemicals) and subjected to agarose gel electrophoresis. Purified DNA segments were then ligated to the isolated Roche expression vector HpaI/NaeI or BclI/NaeI fragment resulting in the final expression vectors. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ (serum-free, suspension culture) 293 Expression System according to the manufacturer's instruction (Invitrogen, USA). Briefly, suspension FreeStyle™ 293-F cells were cultivated in FreeStyle™293 Expression medium at 37° C./8% $CO_2$. Cells were seeded in fresh medium at a density of 1-2×10$^6$ viable cells/ml on the day of transfection. DNA-293Fectin™ complexes (cationic lipid-based formulation for transfecting DNA into cells) were prepared in Opti-MEM® I medium (Minimal Essential Medium (MEM) that allows for a reduction of Fetal Bovine Serum supplementation; Invitrogen, USA) using 325 µl of 293Fectin™ (Invitrogen, Germany) and 250 µg of each plasmid DNA in a 1:1 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Alternatively, antibodies were generated by transient transfection in HEK293-EBNA cells. Antibodies were expressed by transient co-transfection of the respective expression plasmids in adherently growing HEK293-EBNA cells (human embryonic kidney cell line 293 expressing Epstein-Ban-Virus nuclear antigen; American type culture collection deposit number ATCC # CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 µg/ml Geneticin (Gibco). For transfection FuGENE™ (a nonliposomal formulation designed to transfect DNA into cells) Transfection Reagent (Roche Molecular Biochemicals) was used in a ratio of FuGENE™ reagent (µl) to DNA (µg) of 4: 1 (ranging from 3:1 to 6:1). Proteins were expressed from the respective plasmids using an equimolar ratio of plasmids. Cells were fed at day 3 with L-Glutamine and 4 mM, Glucose [Sigma] and NAA [Gibco]. Immunoglobulin variants containing cell culture supernatants were harvested from day 5 to 11 after transfection by centrifugation and stored at −80C. General information regarding the recombinant expression of human immunoglobulins in e.g. HEK293 cells is given in: Meissner, P., et al., Biotechnol. Bioeng. 75 (2001) 197-203.

Purification of Antibodies

Antibodies were purified from cell culture supernatants by affinity chromatography using Protein A SEPHAROSE® (GE Healthcare, Sweden) and SUPERDEX®200 size exclusion chromatography. Briefly, sterile filtered cell culture supernatants were applied on a HITRAP® (prepacked SEPHAROSE®) ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a SUPERDEX®200 HiLoad 120 ml 16/60 or 26/60 gel filtration column (GE Healthcare, Sweden) equilibrated with 20 mM Histidin, 140 mM NaCl, pH 6.0. Fractions containing purified antibodies with less than 5% high molecular weight aggregates were pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-12% Tris-Glycine gels). The aggregate content of antibody samples was analyzed by high-performance SEC using a SUPERDEX® 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. For stability analysis, concentrations of 1 mg/ml of purified proteins were incubated at 4° C. and 40° C. for 7 days and then evaluated by high-performance SEC (e.g. HP SEC Analysis (Purified Protein). The integrity of the amino acid backbone of reduced immunoglobulin variant chains was verified by NanoElectrospray Q-TOF mass spectrometry after removal of N-glycans by enzymatic treatment with Peptide-N-Glycosidase F (Roche Molecular Biochemicals).

Mass Spectrometry

The total deglycosylated mass of antibodies was determined and confirmed via electrospray ionization mass spectrometry (ESI-MS). Briefly, 100 µg purified antibodies were deglycosylated with 50 mU N-Glycosidase F (PNGaseF, ProZyme) in 100 mM $KH_2PO_4/K_2HPO_4$, pH 7 at 37° C. for 12-24 h at a protein concentration of up to 2 mg/ml and subsequently desalted via HPLC on a Sephadex G25 column (GE Healthcare). The mass of the respective antibody chains was determined by ESI-MS after deglycosylation and reduction. In brief, 50 µg antibody in 115 µl were incubated with 60 µl 1M TCEP and 50 µl 8 M Guanidine-hydrochloride subsequently desalted. The total mass and the mass of the reduced antibody chains was determined via ESI-MS on a Q-Star Elite MS system equipped with a NanoMate source. The mass range recorded depends on the samples molecular weight. In general for reduced antibodies the mass range was set from 600-2000 m/z and for non reduced antibodies from 1000-3600 m/z.

SEC-MALLS

SEC-MALLS (size-exclusion chromatography with multi-angle laser light scattering) was used to determine the approximate molecular weight of proteins in solution. According to the light scattering theory, MALLS allows molecular weight estimation of macromolecules irrespective of their molecular shape or other presumptions. SEC-MALLS is based on a separation of proteins according to their size (hydrodynamic radius) via SEC chromatography, followed by concentration- and scattered light-sensitive detectors. SEC-MALLS typically gives rise to molecular weight estimates with an accuracy that allows clear discrimination between monomers, dimers, trimers etc., provided the SEC separation is sufficient.

In this work, the following instrumentation was used: Dionex Ultimate 3000 HPLC; column: SUPEROSE®6 (highly cross-linked, agarose-based size exclusion chromatography media) 10/300 (GE Healthcare); eluent: 1×PBS; flow rate: 0.25 mL/min; detectors: OPTILAB® (refractive index detector) REX (Wyatt Inc., Dernbach), MiniDawn Treos (Wyatt Inc., Dernbach). Molecular weights were calculated with the Astra software, version 5.3.2.13. Protein amounts between 50 and 150 µg were loaded on the column and BSA (Sigma Aldrich) was used as a reference protein.

Dynamic Light Scattering (DLS) Timecourse

Samples (30 µL) at a concentration of approx. 1 mg/mL in 20 mM His/HisCl, 140 mM NaCl, pH 6.0, were filtered via a 384-well filter plate (0.45 µm pore size) into a 384-well optical plate (Corning) and covered with 20 µL paraffin oil (Sigma). Dynamic light scattering data were collected repeatedly during a period of 5 days with a DYNAPRO® DLS plate reader (Wyatt) at a constant temperature of 40° C. Data were processed with DYNAMICS® (software for dynamic light scattering analysis) V6.10 (Wyatt).

Surface Plasmon Resonance

The binding properties of anti-IGF-1R antigen binding proteins and antibodies were analyzed by surface plasmon resonance (SPR) technology using a BIACORE® instrument (Biacore, GE-Healthcare, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR- technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases. For capturing anti-human IgG antibody was immobilized on the surface of a CM5 biosensorchip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 µl/min. Anti-human IgG antibody was injected in sodium acetate, pH 5.0 at 10 µg/ml. A reference control flow cell was treated in the same way but with vehicle buffers only instead of the capturing antibody. Surfaces were blocked with an injection of 1 M ethanolamine/HCl pH 8.5. The IGF-1R antibodies were diluted in HBS-P and injected. All interactions were performed at 25° C. (standard temperature). The regeneration solution of 3 M Magnesium chloride was injected for 60 s at 5 µl/min flow to remove any non-covalently bound protein after each binding cycle. Signals were detected at a rate of one signal per second. Samples were injected at increasing concentrations. FIG. 17 depicts the applied assay format. A low loading density with capturing antibody density and IGF-1R antibody was chosen to enforce binding.

For affinity measurements, human FcgIIIa was immobilized to a CM-5 sensor chip by capturing the His-tagged receptor to an anti-His antibody (Penta-His, Qiagen) which was coupled to the surface by standard amine-coupling and blocking chemistry on a SPR instrument ( BIACORE® T100). After FcgRIIIa capturing, 50 nM IGF1R antibodies were injected at 25° C. at a flow rate of 5 µL/min. The chip was afterwards regenerated with a 60 s pulse of 10 mM glycine-HCl, pH 2.0 solution.

Antibody-dependent Cellular Cytotoxicity Assay (ADCC)

Determination of antibody mediated effector functions by anti-IGF-IR antibodies. In order to determine the capacity of the generated antibodies to elicit immune effector mechanisms antibody-dependent cell cytotoxicity (ADCC) studies were performed. To study the effects of the antibodies in ADCC, DU145 IGF-IR expressing cells (1×10$^6$ cells/ml) were labeled with 1 µl per ml BATDA solution (Perkin Elmer) for 25 minutes at 37° C. in a cell incubator. Afterwards, cells were washed four times with 10 ml of RPMI-FM/PenStrep and spun down for 10 minutes at 200×g. Before the last centrifugation step, cell numbers were determined and cells diluted to 1×10$^5$ cells/ml in RPMI-FM/PenStrep medium from the pellet afterwards. The cells were plated 5,000 per well in a round bottom plate, in a volume of 50 µl. HuMAb antibodies were added at a final concentration ranging from 25-0.1 µg/ml in a volume of 50 µl cell culture medium to 50 µl cell suspension. Subsequently, 50 µl of effector cells, freshly isolated PBMC were added at an E:T ratio of 25:1. The plates were centrifuged for 1 minutes at 200×g, followed by an incubation step of 2 hours at 37° C. After incubation the cells were spun down for 10 minutes at 200×g and 20 µl of supernatant was harvested and transferred to an Optiplate 96-F plate. 200 µl of Europium solution (Perkin Elmer, at room temperature) were added and plates were incubated for 15 minutes on a shaker table. Fluorescence is quantified in a time-resolved fluorometer (Victor 3, Perkin Elmer) using the Eu-TDA protocol from Perkin Elmer. The magnitude of cell lysis by ADCC is expressed as % of the maximum release of TDA fluorescence enhancer from the target cells lysed by detergent corrected for spontaneous release of TDA from the respective target cells.

IGF-1R Internalization Assay

The binding of antibodies and antigen binding protein according the invention to the IGF-1R results in internalization and degradation of the receptor. This process can be monitored by incubating IGF-1R expressing HT29 CRC cells with IGF-1R targeting antibodies followed by a quantification of remaining IGF-1R protein levels in cell lysates by ELISA.

For this purpose, HT29 cells at 1,5×10$^4$ cells/well were incubated in a 96 well MTP in RPMI with 10% FCS over night at 37° C. and 5% CO2 in order to allow attachment of the cells. Next morning, the medium was aspirated and 100 µl anti IGF-1R antibody diluted in RPMI+10% FCS was added in concentrations from 10 nM to 2 pM in 1:3 dilution steps. The cells were incubated with antibody for 18 hours at 37° C. Afterwards, the medium was again removed and 120 µl MES lysis buffer (25 mM MES pH 6.5+Complete) were added.

For ELISA, 96-Well streptavidin coated polystyrene plates (Nunc) were loaded with 100 µl MAK<hu IGF-1Rα>hu-1a-IgG-Bi (Ch. 10) diluted 1:200 in 3% BSA/PBST (final concentration 2.4 µg/ml) and incubated under constant agitation for 1 hour at room temperature. Afterwards, the well content was removed and each well was washed three times with 200 µA PBST. 100 µA of the cell lysate solution were added per well, again incubated for 1 hour at room temperature on a plate shaker, and washed three times with 200 µA PBST. After removal of the supernatant, 100 µl/well PAK<human IGF-1Rα>Ra-C20-IgG (Santa Cruz # sc-713) diluted 1:750 in 3% BSA/PBST was added followed by the same incubation and washing intervals as described above. In order to detect the specific antibody bound to IGF-1R, 100 µl/well of a polyclonal horse-radish-peroxidase-coupled rabbit antibody (Cell Signaling #7074) diluted 1:4000 in 3% BSA/PBST were added. After another hour, unbound antibody was again removed by washing thoroughly 6 times as described above. For quantification of bound antibody, 100 µl/well 3,3'-5,5'-Tetramethylbenzidin (Roche, BM-Blue ID.-Nr.11484281) was added and incubated for 30 minutes at room temperature. The colorigenic reaction is finally stopped by adding 25 µl/well 1M H2SO4 and the light absorption is measured at 450 nm wavelength. Cells not treated with antibody are used as a control for 0% downregulation, lysis buffer as background control.

IGF-1R Autophosphorylation Assay (IGF-1 Stimulation)

Targeting IGF-1R by IGF-1R antibodies results in inhibition of IGF-1 induced autophosphorylation. We investigated the inhibition of autophosphorylation of the wild type IGF-1R MoAb-Dimer compared to the parental IGF-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of IGF-1R antibody or IGF-1R antigen binding protein. After lysis of the cells, the levels of phosphorylated IGF-1R protein were determined by a phospho-IGF-1R specific ELISA, combining a human IGF-1R specific capture antibody and a phospho-Tyrosine specific detection antibody.

Determination of PK Properties: Single Dose Kinetics in Mice

Methods

Animals:

NMRI mice, female, fed, 23-32 g body weight at the time point of compound administration.

Study Protocol:

For a single i.v. dose of 10 mg/kg the mice were allocated to 3 groups with 2-3 animals each. Blood samples are taken from group 1 at 0.5, 168 and 672 hours, from group 2 at 24 and 336 hours and from group 3 at 48 and 504 hours after dosing.

Blood samples of about 100 µL were obtained by retrobulbar puncture. Serum samples of at least 40 µL were obtained from blood after 1 hour at room temperature by centrifugation (9300×g) at room temperature for 2.5 min. Serum samples were frozen directly after centrifugation and stored frozen at −20° C. until analysis.

Analytics:

The concentrations of the human antibodies in mice serum were determined with an enzyme linked immunosorbent assay (ELISA) using 1% mouse serum. Biotinylated monoclonal antibody against human Fcγ (mAb<hFcγ$_{PAN}$>IgG-Bi) was bound to streptavidin coated microtiterplates in the first step. In the next step serum samples (in various dilutions) and reference standards, respectively, were added and bound to the immobilized mAb<hFcγ$_{PAN}$>IgG-Bi. Then digoxigenylated monoclonal antibody against human Fcγ (mAb<hFcγ$_{PAN}$>IgG-Dig) was added. The human antibodies were detected via anti-Dig-horseradish-peroxidase antibody-conjugate. ABTS-solution was used as the substrate for horseradish-peroxidase. The specificity of the used capture and detection antibody, which does not cross react with mouse IgG, enables quantitative determination of human antibodies in mouse serum samples.

Calculations:

The pharmacokinetic parameters were calculated by non-compartmental analysis, using the pharmacokinetic evaluation program WinNonlin™, version 5.2.1.

TABLE 1

Computed Pharmacokinetic Parameters:

| Abbreviations of Pharmacokinetic Parameters | Pharmacokinetic Parameters | Units |
|---|---|---|
| C0 | initial concentration estimated only for bolus IV models | µg/mL |
| C0_NORM | initial concentration estimated only for bolus IV models, dose-normalized | µg/mL/mg/kg |
| T0 | time at initial concentration estimated only for bolus IV models | h |
| TMAX | time of maximum observed concentration | h |
| CMAX | maximum observed concentration, occurring at TMAX | µg/mL |
| CMAX_NORM | Cmax, dose-normalized | µg/mL/mg/kg |
| AUC_0_INF | AUC extrapolated | h * µg/mL |
| AUC_0_LST | AUC observed | h * µg/mL |
| TLAST | Time of last observed concentration >0 | h |
| AUC_0_INF_NORM | AUC extrapolated, dose-normalized | h * µg/mL/mg/kg |
| AUC_0_LST_NORM | AUC observed, dose-normalized | h * µg/mL/mg/kg |
| PCT_AUC_EXTRA | percentage AUC extrapolated | % |
| CL_TOTAL | total clearance | mL/min/kg |
| CL_TOTAL_CTG | total clearance categories | L, M, H |
| VSS | steady state distribution volume | L/kg |
| VSS_CTG | steady state distribution volume categories | L, M, H |
| VZ | terminal distribution volume | L/kg |
| CL/F | total clearance after non IV routes or after IV route of prodrug | mL/min/kg |
| VZ/F | terminal distribution volume after non IV routes or after IV route of prodrug | L/kg |
| MRT_INF | mean residence time (extrapolated) | h |
| MRT_LST | mean residence time (observed) | h |
| HALFLIFE_Z | terminal halflife | h |
| F | bioavailability after non IV routes or after IV route of prodrug | % |

The following pharmacokinetic parameters were used for assessing the human antibodies:

The initial concentration estimated for bolus IV models (C0).

The maximum observed concentration ($C_{max}$), occurring at ($T_{max}$)

The time of maximum observed concentration ($T_{max}$)

The area under the concentration/time curve AUC(0-inf) was calculated by linear trapezoidal rule (with linear interpolation) from time 0 to infinity.

The apparent terminal half-life ($T_{1/2}$) was derived from the equation: $T_{1/2} = \ln 2/\lambda z$.

Total body clearance (CL) was calculated as Dose/AUC (0-inf).

Volume of distribution at steady state (Vss), calculated as MRT(0-inf)×CL (MRT(0-inf), defined as AUMC(0-inf)/AUC(0-inf)).

B. Examples

Example 1

Generation of MoAb-Dimer Antigen Binding Proteins

Figure 2:
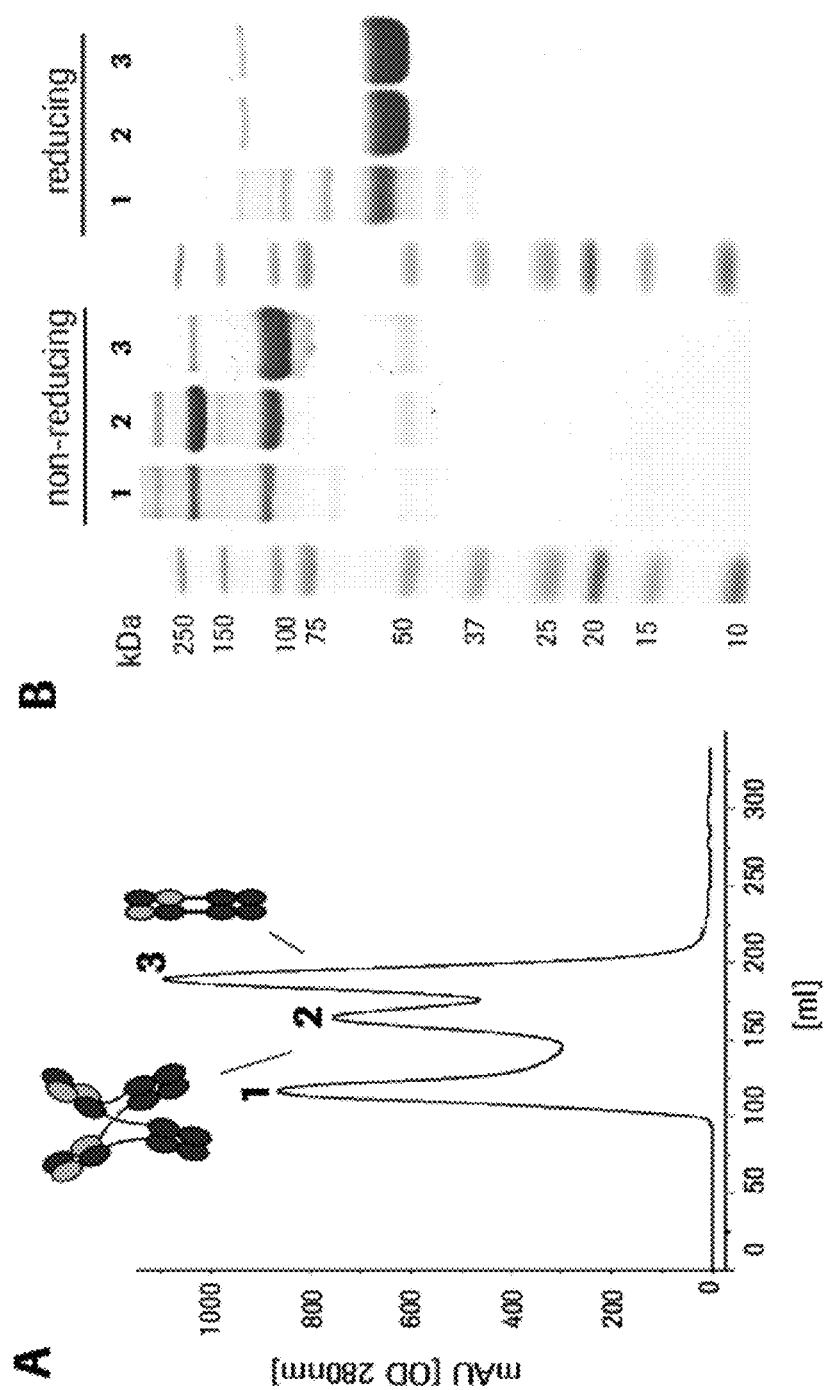
FIG. 2: Biochemical characterization of MoAb-Dimer c-Met (5D5 MoAb-Dimer ("CH3-wt")) (CH3-wt refers to the unchanged, wild type CH3 domain). (A) Protein A purified antibody was separated on an SUPERDEX® (dextran covalently bonded to crosslinked agarose) (200 26/60 column. (B) Peak fractions (1,2,3) were pooled and subjected to SDS-PAGE under non-reducing and reducing conditions. Polyacrylamide gels were stained with Coomassie Blue dye. Individual peaks correspond to MoAb (3), MoAb-Dimer (2) and a higher molecular weight aggregate (1).

We designed antigen binding proteins according to the invention against c-Met (SEQ ID NO:1 and SEQ ID NO:2), IGF-1R (SEQ ID NO:3 and SEQ ID NO:4) and HER3 (SEQ ID NO:5 and SEQ ID NO:6) based on the design principle as shown in FIG. 1A. The respective constructs were transiently expressed in HEK293 cells as described above, and subsequently purified via Protein A affinity chromatography followed by size exclusion. FIGS. 2-4 depict the chromatograms of the size exclusion chromatography of the three different productions of antigen binding proteins as well as the corresponding SDS-PAGE under non-reducing and reducing conditions. In addition to peak 3 in FIG. 2, peak 2 in FIG. 3, peak 3 in FIG. 4 proteins eluting at earlier timepoints from the column peak 2 in FIG. 2, peak 1 in FIG. 3, peak 4 in FIG. 7 were observed. Based on their retention time it was calculated that they exhibited the double the molecular weight of the monovalent antibody (FIG. 1B, MoAb) corresponding to antigen binding protein according to FIG. 1A (MoAb-Dimer).

The size of the two peaks 1 and 2 for the IGF-1R antibodies was confirmed by SEC-MALLS (FIG. 3C) and showed indeed that the protein corresponding to peak 1 exhibited ca. double the molecular weight of the monovalent antibody (peak 2). The existence of a MoAb-Dimer and the identity of the isolated proteins was subsequently confirmed by mass spectrometry. Based on those findings we derived a model for the structure of the MoAb-Dimer that is depicted in FIG. 1A.

We have performed experiments such as mass spectrometry, reduction and protease digestion to confirm the putative structure shown in FIG. 1A.

The stability of the IGF1R AK18 MoAb-Dimer ("CH3-wt") is studied by dynamic light scattering as described above. Briefly, aggregation tendency of the IGF1R AK18 MoAb-Dimer ("CH3-wt") is assessed by a DLS timecourse experiment at 40° C.

Example 2

IGF-1R Binding Affinity

Figure 5:
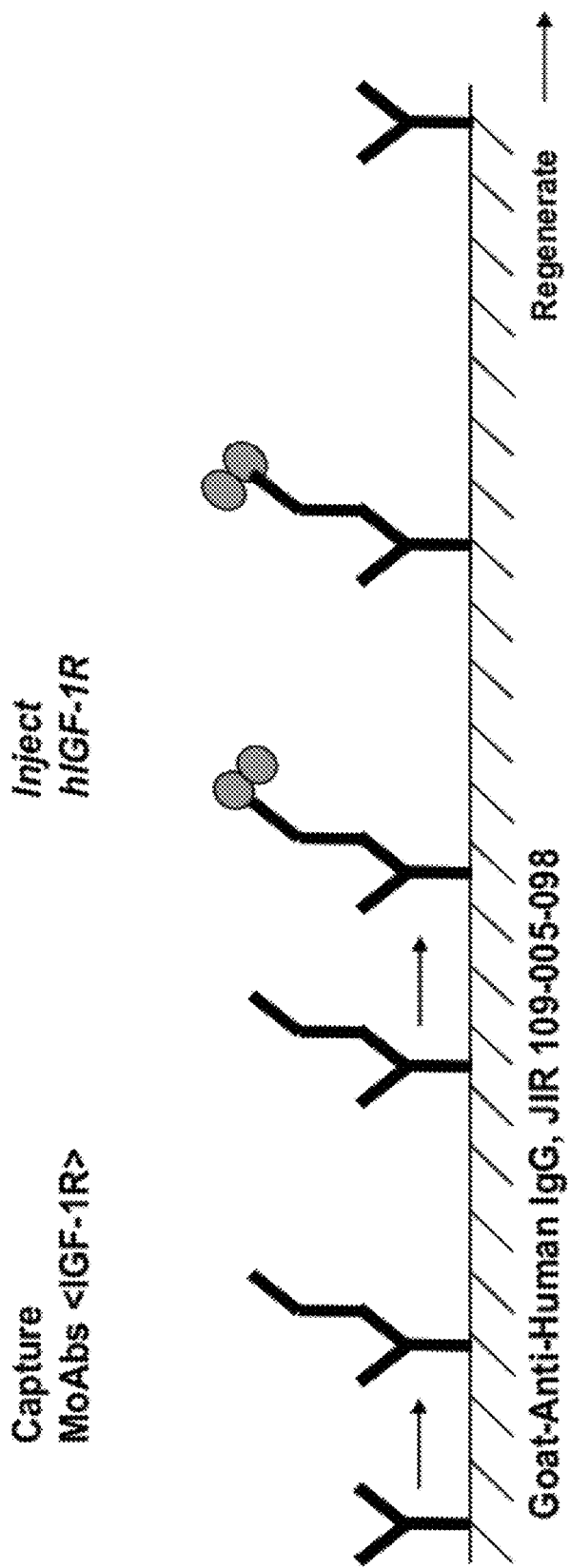
FIG. 5: Schematic picture of the surface plasmon resonance assay applied to analyze the IGF-1R binding affinity. An anti human IgG antibody (JIR 109-005-098) was immobilized on the surface of a CM5 biosensorchip and subsequently captured MoAb or MoAb-Dimer antibodies. Further injection of recombinant IGF-1R ectodomain confirmed functionality of antigen binding sites in MoAb and MoAb-Dimer molecules.

IGF-1R extracellular domain binding of the IGF1R AK18 MoAb-Dimer ("CH3-wt") was compared to the binding of the parental <IGF-1R> IgG1 antibody by surface Plasmon resonance (SPR). FIG. 5 depicts the scheme of the SPR assay to determine the affinity. The analysis (double determination) showed that the IGF-1R binding affinity is retained in the IGF1R AK18 MoAb-Dimer ("CH3-wt").

|                                | k (on)   | k (off)  | KD       |
|--------------------------------|----------|----------|----------|
| Mab (IGF-1R)                   | 1.74E+06 | 6.63E−03 | 3.80E−09 |
| MoAb-Dimer (IGF-1R) (1. deter.)| 1.5E+06  | 3.0E−03  | 2.01E−09 |
| MoAb-Dimer (IGF-1R) (2. deter.)| 1.5E+06  | 3.0E−03  | 2.05E−09 |

Example 3

Cellular Binding to IGF-1R Expressing Cell Lines

Figure 6:
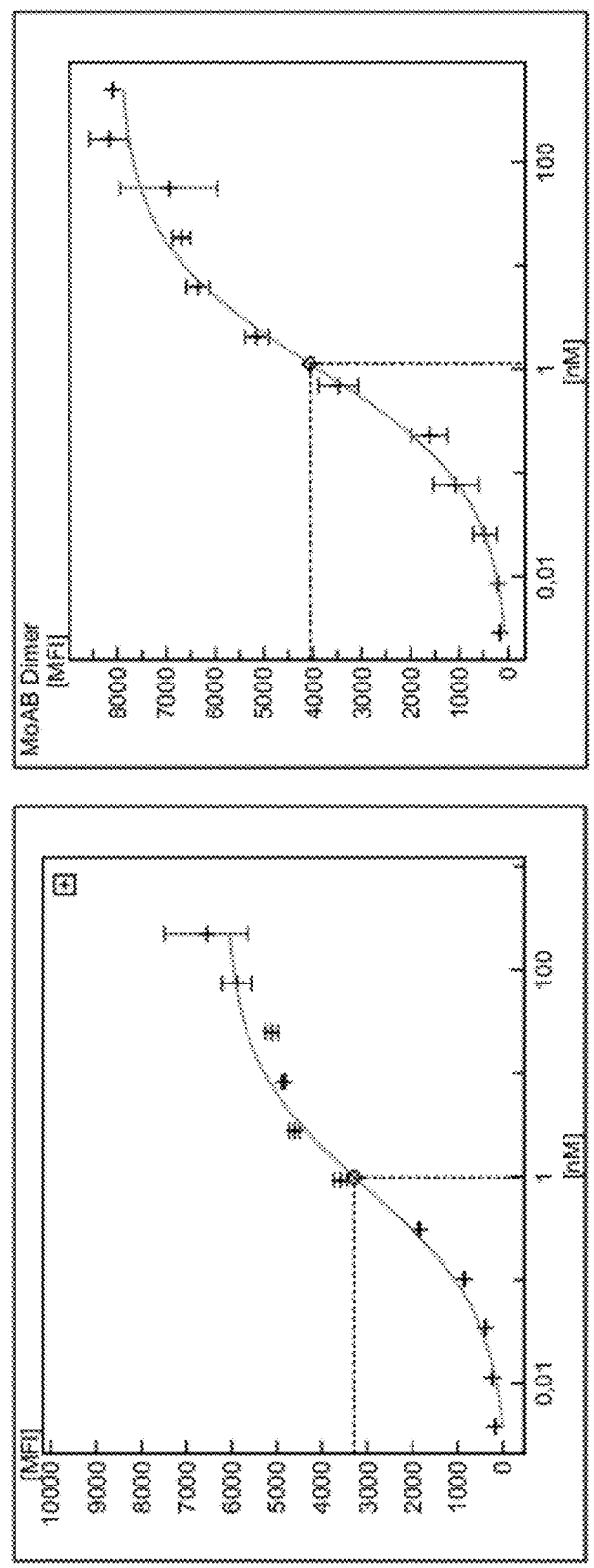
FIG. 6: Cellular binding of MoAb-Dimer (IGF-1R AK18 MoAb-Dimer ("CH3-wt") (B) and parent antibody Mab IGF-1R (A) to A549 cells with flow cytometric analysis. A549 cells were incubated with a dilution series of the indicated antibodies. Bound antibodies were visualized with an Fc-binding secondary fluorophor coupled antibody.

Cellular binding of IGF-1R MoAb-Dimer was demonstrated on A549 cells. A549 cells in the logarithmic growth phase were detached with accutase (Sigma) and 2×10e5 cells were used for each individual antibody incubation. IGF-1R antibody and MoAb-Dimer were added in a three-fold dilution series (100-0.0003 µg/mL). Bound antibodies were visualized with a secondary Alexa488-coupled antibody (5 µg/mL) binding to the constant region of human immunoglobulin. Dead cells were stained with 7-AAD (BD) and excluded from the analysis. Fluorescence intensity of single cells was measured on a FACS Canto (BD Biosciences) flow cytometer. The data show that the MoAb-Dimer showed very similar halfmaximal binding to cells comparable to the parental IGF-1R IgG1 antibody. This implies that the MoAb-Dimer can bind with two arms to IGF-1R on cells and exhibits an avidity effect. However, the total mfi (mean fluorescence intensity) is higher for the MoAb-Dimer than the MAb IGF-1R. This is likely due to the higher number of Fc parts per molecule of IGF-1R on the cell surface. Results are shown in FIG. 6 and below.

Half-Maximal Binding

IGF-1R (150 kDa): 0.76 nM
IGF-1R MoAb-Dimer (200 kDa): 1.13 nM

Example 4

ADCC Induction

Donor-derived peripheral blood mononuclear cells (PBMC) can be used to measure effector cell recruitment by non-glycoengineered and glycoengineered antibodies to cancer cells. Lysis of cancer cells correlates with NK cell mediated cytotoxicity and is proportional to the antibody's ability to recruit NK cells. In this particular setting, DU145 prostate cancer cells were incubated in a 1:25 ratio (DU145: PBMC) ratio with PBMC in the absence or presence of the respective antibodies. After 2 hours cellular lysis was determined using the BATDA/Europium system as described above. The magnitude of cell lysis by ADCC is expressed as % of the maximum release of TDA fluorescence enhancer from the target cells lysed by detergent corrected for spontaneous release of TDA from the respective target cells. The data show that the non-glycoengineered bivalent IGF-1R MoAb-Dimer is superior in inducing ADCC compared to the non-glycoengineered IGF-1R antibody. Surprisingly, the non-glycoengineered IGF-1R MoAb-Dimer is even superior in inducing ADCC at high concentrations compared to the glycoengineered IGF-1R antibody that shows a drop in the ADCC assay going to high concentrations. The superior ADCC induction by the MoAb-Dimer in absence of glycoengineering can be explained by the higher affinity of the construct for FcgRIIIa on NK cells due to bivalency for FcgRIIIa (avidity effect).

Figure 7:
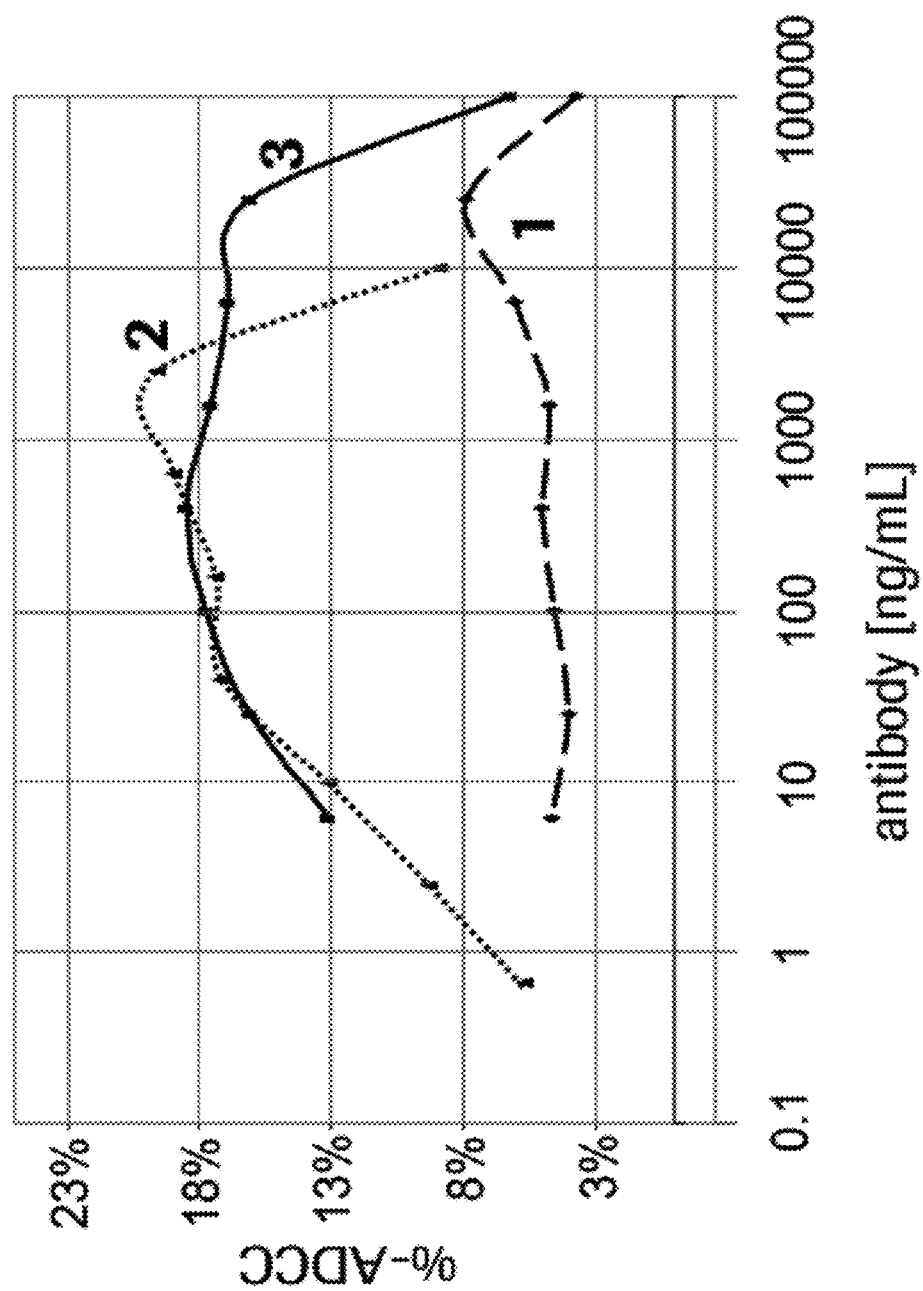
FIG. 7: ADCC Assay with IGF1R Mab non-glycoengineered (non-ge) and glycoengineered (ge) and non-glycoengineered IGF-1R MoAb-Dimer (IGF1R AK18 MoAb-Dimer ("CH3-wt")). Donor derived peripheral blood mononuclear cells (PBMC) were incubated with prostate cancer cells (DU145) in the presence of non-ge IGF1R Mab (1), ge IGF1R Mab (2) and non-ge IGF1R AK18 MoAb-Dimer ("CH3-wt") (3).

Results for non-glycoengineered IGF1R MAb (1), glycoengineered, afucosylated IGF1R MAb (2) and non-ge IGF1R AK18 MoAb-Dimer ("CH3-wt") (3) are presented in FIG. 7, showing that the MoAb-Dimer IGF1R AK18 MoAb-Dimer ("CH3-wt") has improved ADCC compared to the non-glycoengineered IGF MAb and in higher concentrations even compared to glycoengineered, afucosylated IGF1R MAb (2).

Example 5

IGF-1R Internalization Assay

The targeting of IGF-1R on tumor cells by bivalent IGF-1R antibodies results in internalization and lysosomal degradation of IGF-1R. We investigated the internalization properties of the IGF-1R MoAb-Dimer in comparison to the parental IGF-1R parental antibody. For this purpose, HT29 colon cancer cells were treated for 18 hours with different concentrations of MoAb-Dimer and parental IGF-1R antibody. After lysis of the cells, the remaining levels of IGF-1R protein were determined by IGF-1R specific ELISA.

Figure 8:
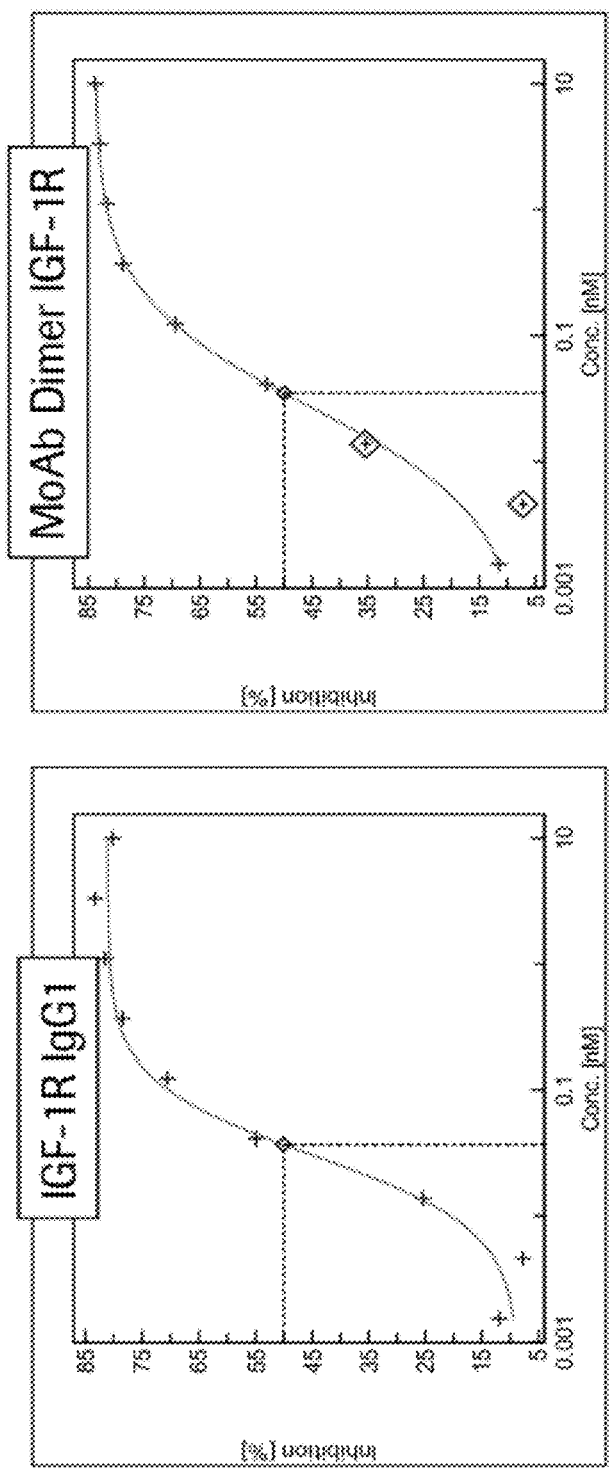
FIG. 8: Internalization of IGF-1R was assessed in HT29 cells following incubation with IGF-1R IgG1 (Mab IGF-1R) antibody and IGF-1R MoAb-Dimer (IGF1R AK18 MoAb-Dimer ("CH3-wt")). The graph depicts total IGF-1R levels upon antibody exposure which were determined in an ELISA-based assay setup.

The data in FIG. 8 show that internalization of IGF-1R by the MoAb-Dimer is virtually identical with the bivalent parental IGF-1R parental antibody. Maximum internalization was 82.99% (IgG1) versus 83.7% (MoAb-Dimer), the concentration required for halfmax inhibition was 0.027 nM (IgG1) versus 0.027 nM (MoAb-Dimer).

Example 6

IGF-1R Autophosphorylation (IGF-1 Stimulation)

Targeting IGF-1R by IGF-1R antibodies results in inhibition of IGF-1 induced autophosphorylation. We investigated the inhibition of autophosphorylation of the MoAb-Dimer IGF-1R antibody compared to the parental IGF-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of IGF-1R antibody and antigen binding protein. After lysis of the cells, the levels of phosphorylated IGF-1R protein were determined by a phospho-IGF-1R specific ELISA, combining a human IGF-1R specific capture antibody and a phospho-Tyrosine specific detection antibody.

Figure 9:
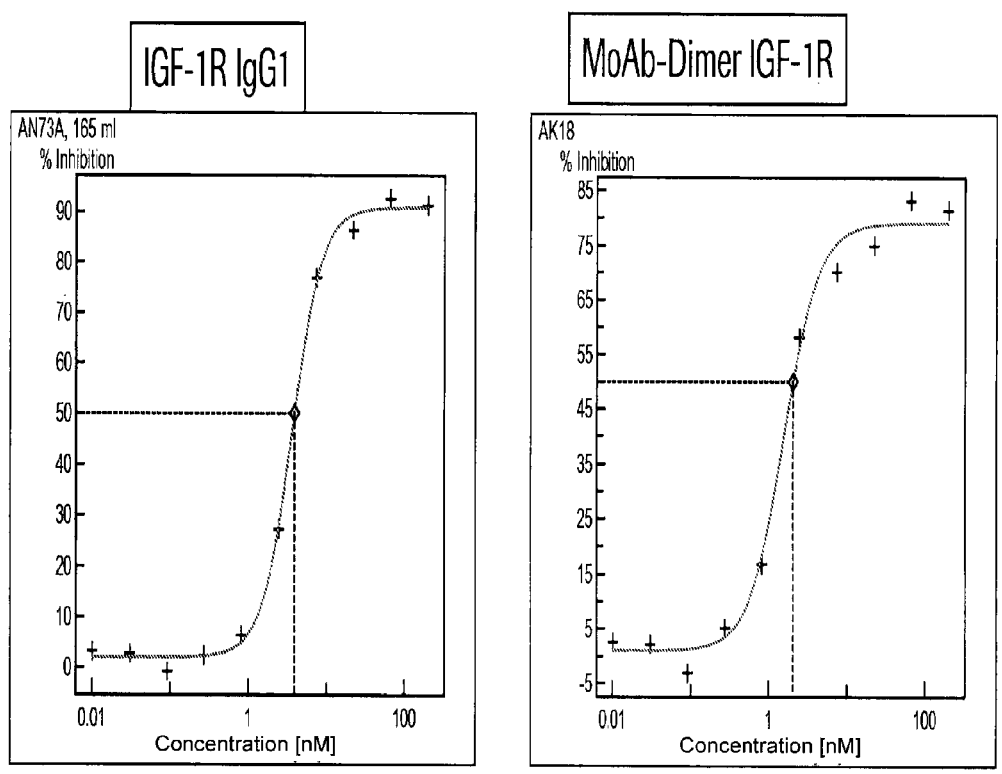
FIG. 9: Autophosphorylation of IGF-1R was assessed following incubation of 3T3-IGF-1R cells with IGF-1R IgG1 antibody and IGF-1R MoAb-Dimer (IGF1R AK18 MoAb-Dimer ("CH3-wt")) in the presence of 10 nM IGF-1. The graph depicts phospho IGF-1R levels upon antibody exposure which were determined in an ELISA-based assay setup.

The data in FIG. 9 shows that the IGF-1R MoAb-Dimer can inhibit IGF-1 induced autophosphorylation similar or even slightly better compared to the IGF-1R IgG1 parental molecule. The concentration required for halfmax inhibition was 1.44 nM (parental IGF-1R IgG1) versus 3.52 nM (MoAb-Dimer), the maximum inhibition observed was 80.3% (parental IGF-1R IgG1) versus 89.1% (MoAb-Dimer).

Example 7

Determination of PK Properties

Pharmacokinetic properties of the antigen binding proteins according to the invention were determined in NMRI mice, female, fed, 23-32 g body weight at the time point of compound administration mice in a single dose PK study, as described above (in the methods sections).

The PK properties are given in the subsequent table and indicate that antigen binding protein IGF1R AK18 MoAb-Dimer ("CH3-wt") has highly valuable PK properties compared to the parental <IGF-1R> IgG1 antibody (like e.g. AUC0-inf, Cmax or C0).

TABLE 2

| | | PK properties | |
|---|---|---|---|
| | | <IGF-1R> IgG1 antibody | <IGF1R> MoAb-Dimer |
| C0 | µg/mL | 81.9 | 201.56 |
| Cmax | µg/mL | 80.7 | 195.9 |
| Tmax | h | 0.5 | 0.5 |
| AUC0-inf | h * µg/mL | 9349 | 12096 |
| term t½ | h | 106.2 | 83.5 |

TABLE 2-continued

| | | PK properties | |
|---|---|---|---|
| | | <IGF-1R> IgG1 antibody | <IGF1R> MoAb-Dimer |
| Cl | mL/min/kg | 0.018 | 0.013 |
| Vss | L/kg | 0.16 | 0.1 |

Example 8

ESI-MS Experiment IGF-1R MoAb-Dimer

The IGF-1R MoAb-Dimer (IGF1R AK18 MoAb ("CH3-wt")) (SEQ ID NO: 3 and SEQ ID NO: 4) was transiently expressed and purified via Protein A affinity and size exclusion chromatography. After preparative SEC (see FIG. 3A) the antibody eluted within two separate peaks, which were collected. Analytical SEC from the first peak (fraction 1) shows an apparent molecular weight of approximately 200 kDa, where as the second peak (fraction 2) corresponds to a molecular weight of 100 kDa. The different molecular weights could be assigned to a defined monomer as by product (fraction 2) and the desired dimer (fraction 1) respectively. SEC-MALS confirmed the initial SEC result and shows for the fraction 2 (monomer) a MW of 99.5 kDa and for the fraction 1 (dimer) a MW of 193.8 kDa.

SDS-PAGE analysis (see FIG. 3B) of the two fractions under denaturing and reducing conditions shows one major band with an apparent molecular weight of 50-60 kDa. Under non reducing conditions fraction 2 shows a major band around a MW of 100 kDa and fraction 1 shows a very broad band ranging from about 100-200 kDa.
Fraction 1=165 mL
Fraction 2=190 mL These initial data show the dimer formation.

ESI-MS spectra (samples incubated with 60 µl 1M TCEP and 50 µL 8 M Guanidine-hydrochloride) of deglycosylated MoAb Dimer from fraction 1 and MoAb monomer fraction 2 show differences. Fraction 2 shows only one peak series corresponding to a monomer with a mass of 98151 Da whereas fraction 1 shows 2 different envelops containing two major peak series corresponding to a mass of 98155 Da (monomer) and a second series with a mass of 196319 Da (dimer).

TABLE 3

Summary of MS data from non reducing ESI-MS measurements from fraction 1 and 2.

| Fraction | Molecular weight, monomer (theor. 98162 Da) | Molecular weight, dimer (theor. 196324 Da) |
|---|---|---|
| Fraction 1 | 98155 Da | 196319 Da |
| Fraction 2 | 98151 Da | Not detected |

The presence of a monomer in fraction 1 may be explained by the incubation conditions (incubated with 60 µl 1M TCEP and 50 µl 8 M Guanidine-hydrochloride) and a potential open S-S bridge between CH1-Ck. In this case, the transfer from an aqueous to an acidic organic solvent during sample preparation for MS can cause the dissociation of the dimer into 2 monomers.

This is in accordance to the results from the CE-SDS (BioAnalyzer) analysis. Fraction 1 contains 71% dimer and 16% monomer under non-reducing conditions. The use of SDS separates non-covalently linked chains. Fraction 2 shows only one monomer signal (98%) under non-reducing conditions.

MS measurements under reducing conditions of fraction 1 and fraction 2 show the correct sequence and expression of the constructs. The MS data from fraction 1 show two different heavy chains with a molecular weight of 47960 Da and 50208 Da in approximately equal amounts. These two heavy chains were also found in fraction 2 with similar intensities.

TABLE 4

Summary of MS data from reducing ESI-MS measurements under reducing conditions from fraction 1 and 2.

| Fraction | Molecular weight, heavy chain 1 (theor. 50226 Da) | Molecular weight, heavy chain 2 (theor. 47961 Da) |
|---|---|---|
| Fraction 1 | 50208 Da (pyro Glu at N-term.) | 47960 Da |
| Fraction 2 | 50211 Da (pyro Glu at N-term.) | 47959 Da |

Example 9

Analysis of MoAb-Dimer Versus Monovalent Monomer Ratios in CH3 Wt and CH3-Modified IGF1R AK18 MoAb-Dimer Antigen Binding Proteins Modifications of the CH3 domains, of the antibody chains can change the ratios of and MoAb-Dimer and MoAb-monomer. Exemplary, different heavy chain modifications were transiently expressed in HEK293F cells together or in combination with the unmodified heavy chain. For comparison, antibody comprising unmodified heavy chains was transiently transfected in parallel. Supernatant containing the antibodies was harvested seven days after transfection. Antibody was precipitated using Protein A sepharose and eluted from the beads with a standard pH shock protocol. Obtained eluates were subjected to a HPLC analysis using a G3000SW (TSKGel) column. Antibody ratios were quantified calculating the area under the respective peaks. The term "CH3-wt" refers to a IgG1 CH3 domain with natural sequence (wild type=wt).

TABLE 5

Figure 10:
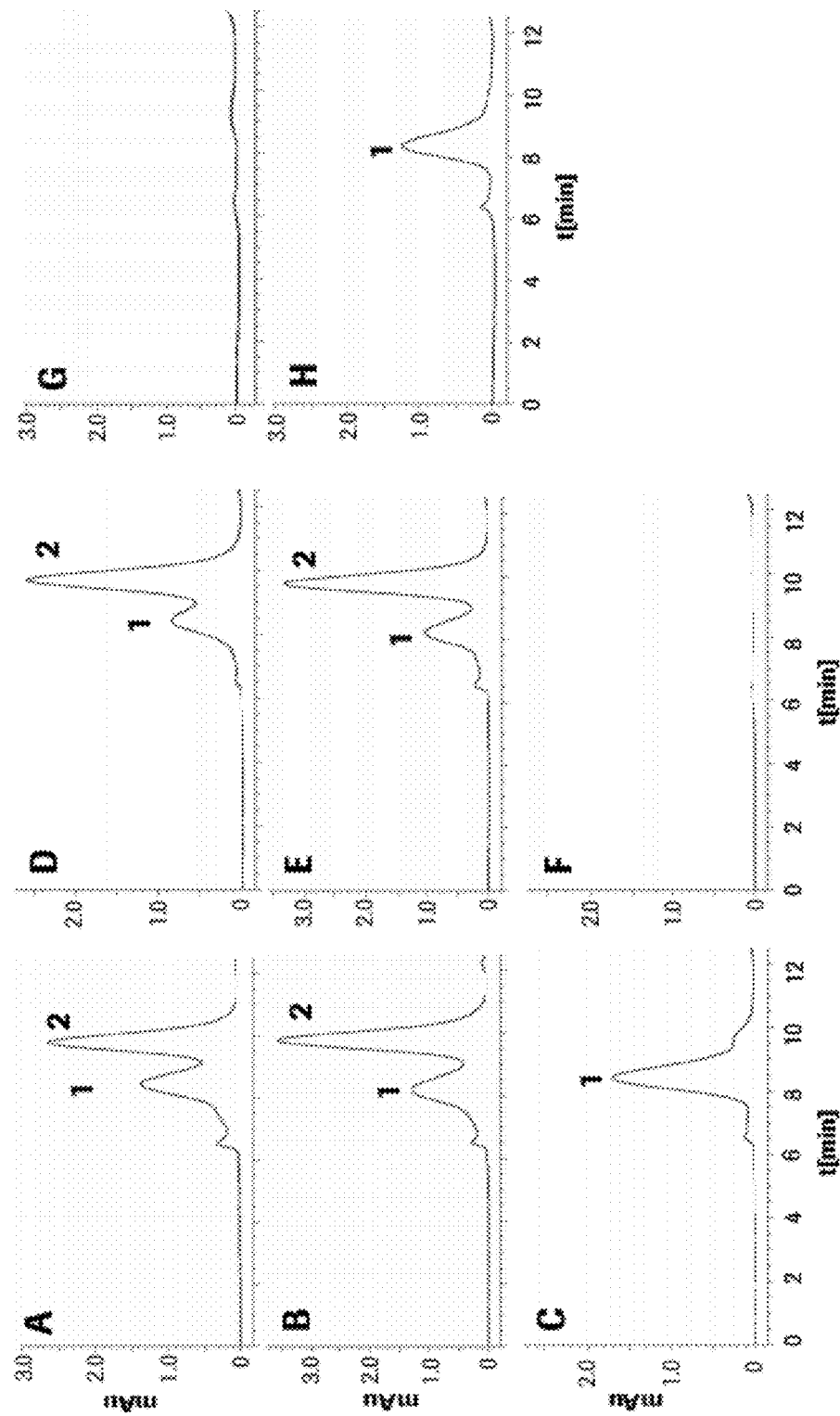
FIG. 10: Analysis of obtained MoAb-Dimer (=antigen binding protein according to the invention) versus MoAb-monomer (=monovalent byproduct) ratios as determined by HPLC. Different antibody with wild type CH3 (CH3-wt) domains and modified CH3 domains were transiently expressed and the ratios of dimer versus monomer determined.
Figure 11:
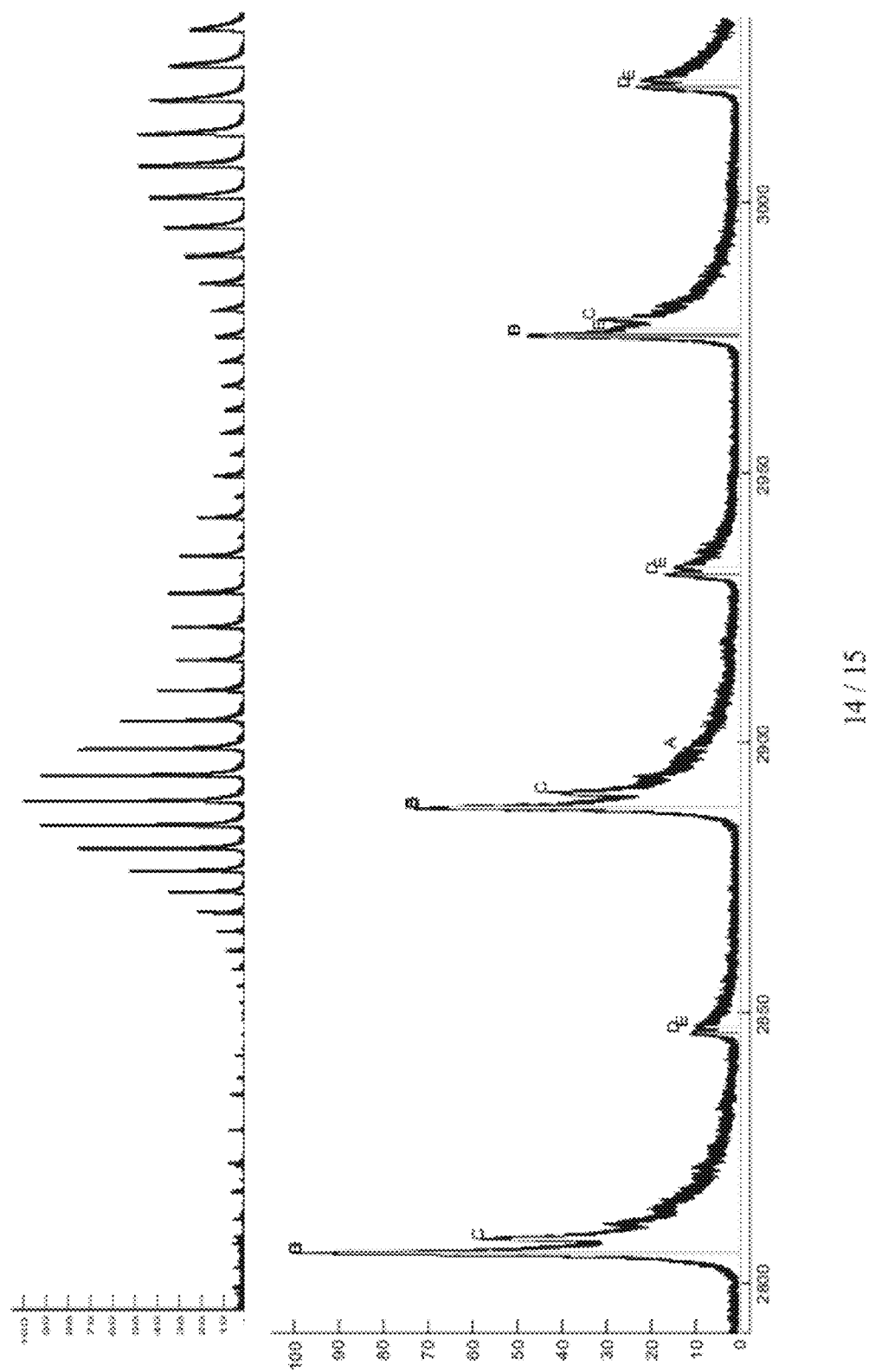
FIG. 11: ESI-MS spectrum of the IGF-1R MoAb Dimer (SEC fraction 1) under non reducing condition and after deglycosylation

Obtained MoAb-dimer (=bivalent antigen binding protein according to the invention) versus MoAb-monomer (=monovalent byproduct) ratios as determined by HPLC. Both desired dimeric product and monomeric byproduct can be easily separated. Values were derived from the chromatograms displayed in FIG. 10.

| Sample | Combination of modified heavy chains a) VL-CH1—CH2—CH3/ b) VH-CL-CH2—CH3 | % Moab-Dimer | % Moab (Monomer) |
|---|---|---|---|
| A | CH3-wt (SEQ ID NO: 3)/CH3-wt (SEQ ID NO: 4) | 30 | 70 |
| B | CH3-wt (SEQ ID NO: 3)/l (SEQ ID NO: 4 with mutations S364F and L368G) | 25 | 75 |
| C | m (SEQ ID NO: 3 with the mutations S364G, L368F, D399K and K409D)/ CH3-wt (SEQ ID NO: 4) | 98.5 | 1.5 |
| D | m (SEQ ID NO: 3 with the mutations S364G, L368F, D399K and K409D)/l (SEQ ID NO: 4 with mutations S364F and L368G) | 17 | 83 |
| E | CH3-wt (SEQ ID NO: 3)/h (SEQ ID NO: 4 with mutations S364W and L368G) | 20 | 80 |
| F | i (SEQ ID NO: 3 with the mutations S364G, L368W, D399K and K409D)/ CH3-wt (SEQ ID NO: 4) | — | — |
| G | i (SEQ ID NO: 3 with the mutations S364G, L368W, D399K and K409D)/h (SEQ ID NO: 4 with mutations S364W and L368G) | — | — |
| H | CH3-IgA ((SEQ ID NO: 7)/CH3-wt (SEQ ID NO: 4) | 100 | 0 | h = mutant with the mutations S364W and L368G in the IgG1 CH3 domain
i = mutant with the mutations S364G, L368W, D399K and K409D in the IgG1 CH3 domain.
l = mutant with the mutations S364F and L368G in the IgG1 CH3 domain
m = mutant with the mutations S364G, L368F, D399K and K409D in the IgG1 CH3 domain.
CH3-wt = IgG1 wt CH3 domain
CH3-IgA = chimer with a IgG1 CH2 domain and IgA CH3 domain Example 10

Production of Glycoengineered Antibodies

For the production of the glycoengineered MoAb antigen binding protein, HEK-EBNA cells are transfected, using the calcium phosphate method, with four plasmids. Two encoding the antibody chains, one for a fusion GnTIII polypeptide expression (a GnT-III expression vector), and one for mannosidase II expression (a Golgi mannosidase II expression vector) at a ratio of 4:4:1:1, respectively. Cells are grown as adherent monolayer cultures in T flasks using DMEM culture medium supplemented with 10% FCS, and are transfected when they are between 50 and 80% confluent. For the transfection of a T150 flask, 15 million cells are seeded 24 hours before transfection in 25 ml DMEM culture medium supplemented with FCS (at 10% V/V final), and cells are placed at 37° C. in an incubator with a 5% $CO_2$ atmosphere overnight. For each T150 flask to be transfected, a solution of DNA, $CaCl_2$ and water is prepared by mixing 94 μg total plasmid vector DNA divided equally between the light and heavy chain expression vectors, water to a final volume of 469 μl and 469 μL of a 1M $CaCl_2$ solution. To this solution, 938 μL of a 50 mM HEPES, 280 mM NaCl, 1.5 mM $Na_2HPO_4$ solution at pH 7.05 are added, mixed immediately for 10 sec and left to stand at room temperature for 20 sec. The suspension is diluted with 10 ml of DMEM supplemented with 2% FCS, and added to the T150 in place of the existing medium. Then additional 13 ml of transfection medium are added. The cells are incubated at 37° C., 5% $CO_2$ for about 17 to 20 hours, then medium is replaced with 25 ml DMEM, 10% FCS. The conditioned culture medium is harvested approx. 7 days post-media exchange by centrifugation for 15 min at 210×g, the solution is sterile filtered (0.22 um filter) and sodium azide in a final concentration of 0.01% w/v is added, and kept at 4° C.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An isolated antigen binding protein comprising a) two modified heavy chains of an antibody which specifically binds to an antigen, wherein VH of each heavy chain is replaced by the VL of said antibody, said modified heavy chains being associated with each other via their CH3 domains of the Fc part; and b) two modified heavy chains of said antibody wherein CH1 of each heavy chain is replaced by CL of said antibody, said modified heavy chains being associated with each other via their CH3 domains of the Fc part;

wherein the VL domains of the heavy chains of a) are associated with the VH domains of the heavy chains of b), and the CH1 domains of the heavy chains of a) are associated with the CL domains of the heavy chains of b);

wherein the antigen-binding protein does not comprise an antibody light chain;

wherein the CH2 and CH3 domains of the Fc part of the modified heavy chains of a) and the CH2 and CH3 domains of the Fc part of the modified heavy chains of b) are of the human IgG1 isotype; and wherein either the two modified heavy chains of a), or the two modified heavy chains of b), are further modified by the amino acid substitutions S364G, L368F, D399K and K409 D, wherein the amino acid positions are numbered according to the EU Index of Kabat, and wherein the other two modified heavy chains comprise wild type CH3 amino acid sequences.

2. The isolated antigen binding protein according to claim 1, characterized in comprising I, a) two modified heavy chains comprising the amino acid sequence of SEQ ID NO:1; and
b) two modified heavy chains comprising the amino acid sequence of SEQ ID NO:2;
wherein either the two modified heavy chains of a) or the two modified heavy chains of b) are further modified by the amino acid substitutions S364G, L368F, D399K and K409D, wherein the amino acid positions are numbered according to the EU Index of Kabat;

II, a) two modified heavy chains comprising the amino acid sequence of SEQ ID NO:3; and
b) two modified heavy chains comprising the amino acid sequence of SEQ ID NO:4;
wherein either the two modified heavy chains of a) or the two modified heavy chains of b) are further modified by the amino acid substitutions S364G, L368F, D399K and K409D, wherein the amino acid positions are numbered according to the EU Index of Kabat;

or

III, a) two modified heavy chains comprising the amino acid sequence of SEQ ID NO:5; and
b) two modified heavy chains comprising the amino acid sequence of SEQ ID NO:6;
wherein either the two modified heavy chains of a) or the two modified heavy chains of b) are further modified by the amino acid substitutions S364G, L368F, D399K and K409D, wherein the amino acid positions are numbered according to the EU Index of Kabat.

3. A pharmaceutical composition comprising an isolated antigen binding protein according to claim 1 and a pharmaceutical carrier.

* * * * *